(12) United States Patent
Musselman

(10) Patent No.: US 10,056,243 B2
(45) Date of Patent: Aug. 21, 2018

(54) APPARATUS AND METHOD FOR RAPID CHEMICAL ANALYSIS USING DIFFERENTIAL DESORPTION

(71) Applicant: IONSENSE INC., Saugus, MA (US)

(72) Inventor: Brian D Musselman, Melrose, MA (US)

(73) Assignee: IONSENSE, INC., Saugus, MA (US)

( * ) Notice: Subject to any disclaimer, the term of this patent is extended or adjusted under 35 U.S.C. 154(b) by 0 days.

(21) Appl. No.: 15/812,913

(22) Filed: Nov. 14, 2017

(65) Prior Publication Data

US 2018/0076015 A1 Mar. 15, 2018

Related U.S. Application Data

(63) Continuation of application No. 15/418,524, filed on Jan. 27, 2017, now Pat. No. 9,824,875, which is a continuation of application No. 15/149,161, filed on May 8, 2016, now Pat. No. 9,558,926, which is a continuation of application No. 14/738,899, filed on Jun. 14, 2015, now Pat. No. 9,337,007.

(60) Provisional application No. 62/024,880, filed on Jul. 15, 2014, provisional application No. 62/012,417, filed on Jun. 15, 2014.

(51) Int. Cl.
  *H01J 49/00* (2006.01)
  *H01J 49/16* (2006.01)
  *H01J 49/04* (2006.01)

(52) U.S. Cl.
  CPC .......... *H01J 49/165* (2013.01); *H01J 49/045* (2013.01)

(58) Field of Classification Search
  CPC .............................. H01J 49/16; H01J 49/0031
  USPC ......................................... 250/281, 282, 288
  See application file for complete search history.

(56) References Cited

U.S. PATENT DOCUMENTS

| | | |
|---|---|---|
| 3,633,027 A | 1/1972 | Rhyage |
| 3,957,470 A | 5/1976 | Dawes |
| 4,016,421 A | 4/1977 | Hull |
| 4,144,451 A | 3/1979 | Kambara |
| 4,213,326 A | 7/1980 | Brodasky |
| 4,542,293 A | 9/1985 | Fenn |
| 4,546,253 A | 10/1985 | Tsuchiya |
| 4,654,052 A | 3/1987 | Sharp |
| 4,662,914 A | 5/1987 | Hansen |

(Continued)

FOREIGN PATENT DOCUMENTS

| | | |
|---|---|---|
| DE | 102007015542 | 10/2007 |
| EP | 1434050 | 6/2004 |

(Continued)

OTHER PUBLICATIONS

The AccuTOF-DART Mass Spectrometer, Jan. 1, 2006, pp. 1-6; www.jeolusa.com/SERVICESUPPORT/ApplicationsResources/AnalyticalInstruments/Documents/Downloads/tabid/337/DMXModule/693/CommandCore_Download/Default.aspx?EntryId=171.

(Continued)

*Primary Examiner* — Michael Maskell
(74) *Attorney, Agent, or Firm* — Sci-Law Strategies, PC

(57) ABSTRACT

The present invention is directed to a method and device to generate a chemical signature for a mixture of analytes. The present invention involves using a SPME surface to one or both absorb and adsorb the mixture of analytes. In an embodiment of the invention, the surface is then exposed to different temperature ionizing species chosen with appropriate spatial resolution to desorb a chemical signature for the mixture of analytes.

22 Claims, 24 Drawing Sheets

(56) References Cited

U.S. PATENT DOCUMENTS

| | | |
|---|---|---|
| 4,861,988 A | 8/1989 | Henion |
| 5,012,052 A | 4/1991 | Hayes |
| 5,055,677 A | 10/1991 | Amirav |
| 5,137,553 A | 8/1992 | Dawes |
| 5,192,865 A | 3/1993 | Zhu |
| 5,306,412 A | 4/1994 | Whitehouse |
| 5,352,892 A | 10/1994 | Mordehai |
| 5,367,163 A | 11/1994 | Otsuka |
| 5,381,008 A | 1/1995 | Tanner |
| 5,412,208 A | 5/1995 | Covey |
| 5,448,062 A | 9/1995 | Cooks |
| 5,552,599 A | 9/1996 | Giessmann |
| 5,559,326 A | 9/1996 | Goodley |
| 5,614,711 A | 3/1997 | Li |
| 5,624,537 A | 4/1997 | Turner |
| 5,684,300 A | 11/1997 | Taylor |
| 5,716,825 A | 2/1998 | Hancock |
| 5,736,741 A | 4/1998 | Bertsch |
| 5,788,166 A | 8/1998 | Valaskovic |
| 5,859,433 A | 1/1999 | Franzen |
| 5,868,322 A | 2/1999 | Loucks, Jr. |
| 5,877,495 A | 3/1999 | Takada |
| 5,889,404 A | 3/1999 | Abdel-Rahman |
| 5,959,297 A | 9/1999 | Weinberg |
| 5,997,746 A | 12/1999 | Valaskovic |
| 6,085,601 A | 7/2000 | Linker |
| 6,107,628 A | 8/2000 | Smith |
| 6,124,675 A | 9/2000 | Betrand |
| 6,190,559 B1 | 2/2001 | Valaskovic |
| 6,225,623 B1 | 5/2001 | Turner |
| 6,297,499 B1 | 10/2001 | Fenn |
| 6,359,275 B1 | 3/2002 | Bertsch |
| 6,395,183 B1 | 5/2002 | Valaskovic |
| 6,562,211 B1 | 5/2003 | Kunnecke |
| 6,583,408 B2 | 6/2003 | Smith |
| 6,600,155 B1 | 7/2003 | Andrien, Jr. |
| 6,646,256 B2 | 11/2003 | Gourley |
| 6,649,907 B2 | 11/2003 | Ebeling |
| 6,670,608 B1 | 12/2003 | Taylor |
| 6,690,006 B2 | 2/2004 | Valaskovic |
| 6,713,757 B2 | 3/2004 | Tanner |
| 6,717,139 B2 | 4/2004 | Taniguchi |
| 6,723,985 B2 | 4/2004 | Schultz |
| 6,744,041 B2 | 6/2004 | Sheehan |
| 6,744,046 B2 | 6/2004 | Valaskovic |
| 6,753,523 B1 | 6/2004 | Whitehouse |
| 6,784,424 B1 | 8/2004 | Willoughby |
| 6,794,642 B2 | 9/2004 | Bateman et al. |
| 6,803,565 B2 | 10/2004 | Smith |
| 6,806,468 B2 | 10/2004 | Laiko |
| 6,818,889 B1 | 11/2004 | Sheehan |
| 6,861,647 B2 | 3/2005 | Reilly |
| 6,875,980 B2 | 4/2005 | Bateman |
| 6,878,930 B1 | 4/2005 | Willoughby |
| 6,888,132 B1 | 5/2005 | Sheehan |
| 6,914,243 B2 | 7/2005 | Sheehan |
| 6,943,347 B1 | 9/2005 | Willoughby |
| 6,949,739 B2 | 9/2005 | Franzen |
| 6,949,740 B1 | 9/2005 | Sheehan |
| 6,949,741 B2 | 9/2005 | Cody |
| 6,956,205 B2 | 10/2005 | Park |
| 6,977,372 B2 | 12/2005 | Valaskovic |
| 6,979,816 B2 | 12/2005 | Tang |
| 6,987,264 B1 | 1/2006 | Whitehouse |
| 6,992,299 B2 | 1/2006 | Lee |
| 7,015,466 B2 | 3/2006 | Takats |
| 7,019,289 B2 | 3/2006 | Wang |
| 7,034,292 B1 | 4/2006 | Whitehouse |
| 7,041,972 B2 | 5/2006 | Bajic |
| 7,049,584 B1 | 5/2006 | Whitehouse |
| 7,053,368 B2 | 5/2006 | Thakur |
| 7,064,317 B2 | 6/2006 | McLuckey |
| 7,071,464 B2 | 7/2006 | Reinhold |
| 7,081,618 B2 | 7/2006 | Laprade |
| 7,081,621 B1 | 7/2006 | Willoughby |
| 7,095,019 B1 | 8/2006 | Sheehan |
| 7,098,452 B2 | 8/2006 | Schneider |
| 7,112,785 B2 | 9/2006 | Laramee |
| 7,138,626 B1 | 11/2006 | Karpetsky |
| 7,157,698 B2 | 1/2007 | Makarov |
| 7,161,145 B2 | 1/2007 | Oser |
| 7,196,525 B2 | 3/2007 | Sparkman |
| 7,247,495 B2 | 7/2007 | Amirav |
| 7,253,406 B1 | 8/2007 | Sheehan |
| 7,332,345 B2 | 2/2008 | Darrach |
| 7,423,261 B2 | 9/2008 | Truche |
| 7,429,731 B1 | 9/2008 | Karpetsky |
| 7,462,826 B2 | 12/2008 | Schneider |
| 7,544,933 B2 | 6/2009 | Cooks |
| 7,569,812 B1 | 8/2009 | Karpetsky |
| 7,582,864 B2 | 9/2009 | Verentchikov |
| 7,700,913 B2 | 4/2010 | Musselman |
| 7,705,297 B2 | 4/2010 | Musselman |
| 7,714,281 B2 | 5/2010 | Musselman |
| 7,772,546 B2 | 8/2010 | Jackson |
| 7,777,181 B2 | 8/2010 | Musselman |
| 7,858,926 B1 | 12/2010 | Whitehouse |
| 7,893,408 B2 | 2/2011 | Hieftje |
| 7,915,579 B2 | 3/2011 | Chen |
| 7,923,681 B2 | 4/2011 | Collings |
| 7,928,364 B2 | 4/2011 | Musselman |
| 7,929,138 B1 | 4/2011 | Webb |
| 7,982,183 B2 | 7/2011 | Marakov |
| 7,982,185 B2 | 7/2011 | Whitehouse |
| 8,003,935 B2 | 8/2011 | Robinson |
| 8,026,477 B2 | 9/2011 | Musselman |
| 8,044,346 B2 | 10/2011 | Kostiainen |
| RE43,078 E | 1/2012 | Cody |
| 8,101,910 B2 | 1/2012 | Loboda |
| 8,207,497 B2 | 6/2012 | Musselman |
| 8,217,341 B2 | 7/2012 | Musselman |
| 8,242,459 B2 | 8/2012 | Sun |
| 8,278,619 B2 | 10/2012 | Makarov |
| 8,304,718 B2 | 11/2012 | Ouyang |
| 8,308,339 B2 | 11/2012 | Karpetsky |
| 8,334,507 B1 | 12/2012 | Whitehouse |
| 8,362,418 B2 | 1/2013 | Xu |
| 8,410,431 B2 | 4/2013 | Ouyang |
| 8,421,005 B2 | 4/2013 | Musselman |
| 8,440,965 B2 | 5/2013 | Musselman |
| 8,481,922 B2 | 7/2013 | Musselman |
| 8,497,474 B2 | 7/2013 | Musselman |
| 8,519,354 B2 | 8/2013 | Charipar |
| 8,525,109 B2 | 9/2013 | Musselman |
| 8,563,945 B2 | 10/2013 | Musselman |
| RE44,603 E | 11/2013 | Cody |
| 8,592,756 B2 | 11/2013 | Ouyang |
| 8,592,758 B1 | 11/2013 | Nilles |
| 8,604,423 B2 | 12/2013 | Enke |
| 8,648,295 B2 | 2/2014 | Enke |
| 8,664,000 B2 | 3/2014 | Yang |
| 8,686,351 B2 | 4/2014 | Ouyang |
| 8,704,167 B2 | 4/2014 | Cooks |
| 8,710,437 B2 | 4/2014 | Cooks |
| 8,729,496 B2 | 5/2014 | Musselman |
| 8,754,365 B2 | 6/2014 | Krechmer |
| 8,766,178 B2 | 7/2014 | Ouyang |
| 8,803,085 B2 | 8/2014 | Ouyang |
| 8,816,275 B2 | 8/2014 | Ouyang |
| 8,822,949 B2 | 9/2014 | Musselman |
| 8,853,627 B2 | 10/2014 | Ouyang |
| 8,859,956 B2 | 10/2014 | Ouyang |
| 8,859,957 B2 | 10/2014 | Ouyang |
| 8,859,958 B2 | 10/2014 | Ouyang |
| 8,859,959 B2 | 10/2014 | Ouyang |
| 8,890,063 B2 | 11/2014 | Ouyang |
| 8,895,916 B2 | 11/2014 | Musselman |
| 8,895,918 B2 | 11/2014 | Cooks |
| 8,927,926 B2 | 1/2015 | Shimada |
| 8,932,875 B2 | 1/2015 | Cooks |
| 8,933,398 B2 | 1/2015 | Ouyang |
| 8,937,288 B1 | 1/2015 | Cooks |
| 8,963,079 B2 | 2/2015 | Ouyang |
| 8,963,101 B2 | 2/2015 | Krechmer |

(56) References Cited

U.S. PATENT DOCUMENTS

| | | | |
|---|---|---|---|
| 9,024,254 B2 | 5/2015 | Cooks | |
| 9,064,674 B2 | 6/2015 | Ouyang | |
| 9,105,435 B1 | 8/2015 | Musselman | |
| 9,116,154 B2 | 8/2015 | Ouyang | |
| 9,159,540 B2 | 10/2015 | Ouyang | |
| 9,165,752 B2 | 10/2015 | Cooks | |
| 9,224,587 B2 | 12/2015 | Musselman | |
| 9,230,792 B2 | 1/2016 | Cooks | |
| 9,337,007 B2 | 5/2016 | Musselman | |
| 9,484,195 B2 | 11/2016 | Ouyang | |
| 9,500,630 B2 | 11/2016 | Cooks | |
| 9,514,923 B2 | 12/2016 | Krechmer | |
| 9,538,945 B2 | 1/2017 | Cooks | |
| 9,546,979 B2 | 1/2017 | Cooks | |
| 9,548,192 B2 | 1/2017 | Cooks | |
| 9,551,079 B2 | 1/2017 | Cooks | |
| 9,558,926 B2 | 1/2017 | Musselman | |
| 9,607,306 B2 | 3/2017 | Hieftje | |
| RE46,366 E | 4/2017 | Cody | |
| 9,620,344 B2 | 4/2017 | Cooks | |
| 9,700,251 B2 | 7/2017 | Cooks | |
| 9,704,700 B2 | 7/2017 | Cooks | |
| 9,719,181 B2 | 8/2017 | Cooks | |
| 9,733,228 B2 | 8/2017 | Cooks | |
| 2002/0121596 A1 | 9/2002 | Laiko | |
| 2002/0121598 A1 | 9/2002 | Park | |
| 2002/0162967 A1 | 11/2002 | Atkinson | |
| 2002/0185593 A1 | 12/2002 | Doring | |
| 2002/0185595 A1 | 12/2002 | Smith | |
| 2002/0185606 A1 | 12/2002 | Smith | |
| 2003/0052268 A1 | 3/2003 | Doroshenko | |
| 2004/0094706 A1 | 5/2004 | Covey | |
| 2004/0129876 A1 | 7/2004 | Franzen | |
| 2004/0159784 A1 | 8/2004 | Doroshenko | |
| 2005/0230635 A1 | 10/2005 | Takats | |
| 2005/0236374 A1 | 10/2005 | Blankenship | |
| 2006/0266941 A1 | 11/2006 | Vestal | |
| 2007/0114389 A1 | 5/2007 | Karpetsky | |
| 2007/0228271 A1 | 10/2007 | Truche | |
| 2008/0156985 A1 | 7/2008 | Venter | |
| 2008/0202915 A1 | 8/2008 | Hieftje | |
| 2008/0217254 A1 | 9/2008 | Anderson | |
| 2009/0090197 A1* | 4/2009 | Finlay | G01N 1/2214 73/863.12 |
| 2009/0090858 A1 | 4/2009 | Musselman | |
| 2010/0078550 A1 | 4/2010 | Wiseman | |
| 2010/0140468 A1* | 6/2010 | Musselman | H01J 49/0404 250/282 |
| 2011/0215798 A1 | 9/2011 | Beer | |
| 2012/0006983 A1 | 1/2012 | Cody | |
| 2012/0068063 A1* | 3/2012 | Fernandez | G01N 27/622 250/282 |
| 2012/0145890 A1 | 6/2012 | Goodlett | |
| 2012/0199735 A1* | 8/2012 | Krechmer | H01J 49/049 250/286 |
| 2012/0208004 A1 | 8/2012 | Wolcott | |
| 2012/0223226 A1 | 9/2012 | Rafferty | |
| 2012/0312980 A1 | 12/2012 | Whitehouse | |
| 2012/0322683 A1 | 12/2012 | Liu | |
| 2013/0020482 A1 | 1/2013 | Enke | |
| 2013/0037710 A1 | 2/2013 | Wu | |
| 2013/0092832 A1 | 4/2013 | Enke | |
| 2013/0273552 A1 | 10/2013 | Ohashi | |
| 2013/0284915 A1 | 10/2013 | Shimada | |
| 2013/0299688 A1* | 11/2013 | Balogh | H01J 49/168 250/282 |
| 2014/0024822 A1 | 1/2014 | Connolly | |
| 2016/0314956 A1 | 10/2016 | Cooks | |
| 2017/0082604 A1 | 3/2017 | Ouyang | |
| 2017/0084438 A1 | 3/2017 | Cooks | |
| 2017/0103879 A1 | 4/2017 | Cooks | |
| 2017/0130352 A1 | 5/2017 | Cooks | |
| 2017/0135613 A1 | 5/2017 | Cooks | |
| 2017/0148622 A1 | 5/2017 | Musselman | |
| 2017/0154761 A1 | 6/2017 | Ouyang | |
| 2017/0168032 A1 | 6/2017 | Cooks | |
| 2017/0221695 A1 | 8/2017 | Cooks | |
| 2017/0229299 A1 | 8/2017 | Musselman | |
| 2017/0248607 A1 | 8/2017 | Cooks | |
| 2017/0273605 A1 | 9/2017 | Cooks | |
| 2017/0287690 A1 | 10/2017 | Cooks | |
| 2017/0309462 A1 | 10/2017 | Cooks | |

FOREIGN PATENT DOCUMENTS

| | | |
|---|---|---|
| GB | 2263578 | 7/1993 |
| JP | 50-106694 | 8/1975 |
| JP | 51-120288 | 10/1976 |
| JP | 52-91494 | 8/1977 |
| JP | 60-41748 | 3/1985 |
| JP | 2003185635 | 7/2003 |
| JP | 2003222574 | 8/2003 |
| JP | 2005-150027 | 6/2005 |
| JP | 2007525677 | 6/2007 |
| JP | 2009539114 | 11/2009 |
| WO | WO03025973 | 3/2003 |
| WO | WO03081205 | 10/2003 |
| WO | WO2004068131 | 8/2004 |
| WO | WO2005094389 | 10/2005 |
| WO | WO2008054393 | 5/2008 |
| WO | WO2008082603 | 7/2008 |
| WO | WO2015195599 | 12/2015 |
| WO | WO2016145041 | 9/2016 |
| WO | WO2017040359 | 3/2017 |
| WO | WO2017053911 | 3/2017 |
| WO | WO2017070478 | 4/2017 |
| WO | WO2017079193 | 5/2017 |
| WO | WO2017127670 | 7/2017 |
| WO | WO2017132444 | 8/2017 |
| WO | WO2017180871 | 10/2017 |

OTHER PUBLICATIONS

Cody, R.B. et al., "Versatile New Ion Source for the Analysis of Materials in Open Air under Ambient Conditions" Anal. Chem., 2005, 77, 2297-2302.

Cooks, R.G. et al., "Ambient Mass Spectrometry", Science, 2006, 311, 1566-1570.

Dalton, C.N. et al., "Electrospray-Atmospheric Sampling Glow Discharge Ionization Source for the Direct Analysis of Liquid Samples", Analytical Chemistry, Apr. 1, 2003, vol. 75, No. 7, pp. 1620-1627.

Garimella, S. et al., "Gas-flow assisted ion transfer for mass spectrometry", J. Mass Spectrom. 2012, 17, 201-207.

Guzowski, J.P. Jr. et al., "Development of a Direct Current Gas Sampling Glow Discharge Ionization Source for the Time-of-Flight Mass Spectrometer", J. Anal. At. Spectrom., 14, 1999, pp. 1121-1127.

Haddad, R., et al., "Easy Ambient Sonic-Spray Ionization Mass Spectrometry Combined with Thin-Layer Chromatography," Analytical Chemistry, vol. 80, No. 8, Apr. 15, 2008, pp. 2744-2750.

Harris, Glenn A. et al., Ambient Sampling/Ionization Mass Spectrometry: Applications and Current Trends, Apr. 15, 2011, Anal. Chem. 2011, 83, pp. 4508-4538.

Harris, Glenn A. et al., Simulations and Experimental Investigation of Atmospheric Transport in an Ambient Metastable-Induced Chemical Ionization Source, Anal. Chem. 2009, 81, pp. 322-329.

Hill, C.A. et al., "A pulsed corona discharge switchable high resolution ion mobility spectrometer-mass spectrometer", Analyst, 2003, 128, pp. 55-60.

Hiraoka, K. et al., "Atmospheric-Pressure Penning Ionization Mass Spectrometry", Rapid Commun. Mass Spectrom., 18, 2004, pp. 2323-2330.

McLuckey, S.A. et al., "Atmospheric Sampling Glow Discharge Ionization Source for the Determination of Trace Organic Compounds in Ambient Air", Anal. Chem., 60, 1988, pp. 2220-2227.

Otsuka, K. et al., "An Interface for Liquid Chromatograph/Liquid Ionization Mass Spectrometer", Analytical Sciences, Oct. 1988, vol. 4, pp. 467-472.

(56) References Cited

OTHER PUBLICATIONS

Takáts et al., "Mass Spectrometry Sampling Under Ambient Conditions with Desorption Electrospray Ionization," Science, vol. 306, No. 5695, Oct. 15, 2004, pp. 471-473.
Tembreull, R., et al., "Pulsed Laser Desorption with Resonant Two-Photon Ionization Detection in Supersonic Beam Mass Spectrometry," Anal. Chem., vol. 58, 1986, pp. 1299-1303, p. 1299.
Zhao, J. et al., Liquid Sample Injection Using an Atmospheric Pressure Direct Current Glow Discharge Ionization Source, Analytical Chemistry, Jul. 1, 1992, vol. 64, No. 13, pp. 1426-1433.
International Search Report, Application No. PCT/US2007/63006, dated Feb. 5, 2008, 8 pages.
Extended European Search Report, Application No. 07757665.0 PCT/US2007/063006 dated Jan. 7, 2010, 8 pages.
Article 94(3) European Communication, Application No. 07757665.0 PCT/US2007/063006, dated Mar. 14, 2012, 9 pages.
International Search Report, Application No. PCT/US2007/69823, dated Feb. 15, 2008, 8 pages.
Extended European Search Report, Application No. 07797812.0 PCT/US2007/069823, dated Apr. 4, 2010, 9 pages.
Article 94(3) European Communication, Application No. 07797812.0 PCT/US2007/069823, dated Jul. 27, 2012, 9 pages.
International Search Report, Application No. PCT/US2007/69821, dated Feb. 7, 2008.
Extended European Search Report, Application No. 07797811.2 PCT/US2007/069821, dated Mar. 25, 2010, 9 pages.
European Summons, Application No. 07797811.2 PCT/US2007/069821, Feb. 18, 2013, 8 pages.
International Search Report, Application No. PCT/US2007/81439, dated Mar. 20, 2008, 9 pages.
Extended European Search Report, Application No. 07844307.4 PCT/US2007/081439, dated Apr. 14, 2010, 12 pages.
Japanese Office Action, Application No. 2008-558459 PCT/US2007/063006, dated Jan. 19, 2012, 4 pages.
Unofficial Translation of Japanese Office Action, Application No. 2008-558459 PCT/US2007/063006, dated Jan. 19, 2012, 5 pages.
Chinese Office Action, Application No. 200780015974.5 PCT/US2007/063006, dated Feb. 2, 2012, 5 pages.
Chinese Office Action, Application No. 200780015974.5 PCT/US2007/063006, dated Sep. 25, 2012, 8 pages.
Chinese Office Action, Application No. 200780015974.5 PCT/US2007/063006, dated Dec. 26, 2012, 7 pages.
International Search Report, Application No. PCT/US2012/000061, dated Aug. 6, 2013, 8 pages.
Oral Proceedings European Communication, Application No. 07757665.0 PCT/US2007/063006, dated Sep. 3, 2013, 5 pages.
Korean Patent Application 7024130/2008 Office Action, dated Jun. 29, 2013, 3 pages.
Korean Patent Application 7024130/2008 Office Action, translation, dated Jun. 29, 2013, 3 pages.
Article 94(3) European Communication, Application No. 07797811.2 PCT/US2007/069821, dated Feb. 2, 2012, 8 pages.
Summons Application No. 07797811.2 PCT/US2007/069821, Feb. 18, 2013, 10 pages.
Chinese Office Action, Application No. 201280003101.3 PCT/US12/00061, dated Jan. 22, 2016, 3 pages.
Translation of Chinese Office Action, Application No. 201280003101.3 PCT/US12/00061, dated Jan. 22, 2016, 18 pages.
Japanese Office Action, Application No. 2013552527 PCT/US12/00061, dated Jan. 22, 2016, 3 pages.
Translation of Japanese Office Action, Application No. 2013552527 PCT/US12/00061, dated Jan. 22, 2016, 4 pages.
Extended European Search Report, Application No. 12742544.5 PCT/US20012/0000061, dated Sep. 12, 2017, 9 pages.
Gibbons, J.R., 'Variable Heating Rate Wire Mesh Pyrolysis Apparatus' Rev. Sci. Instr. 60 (1989) pp. 1129-1139.

* cited by examiner

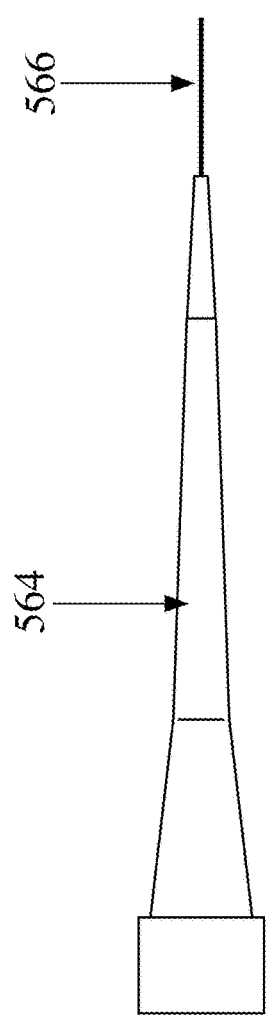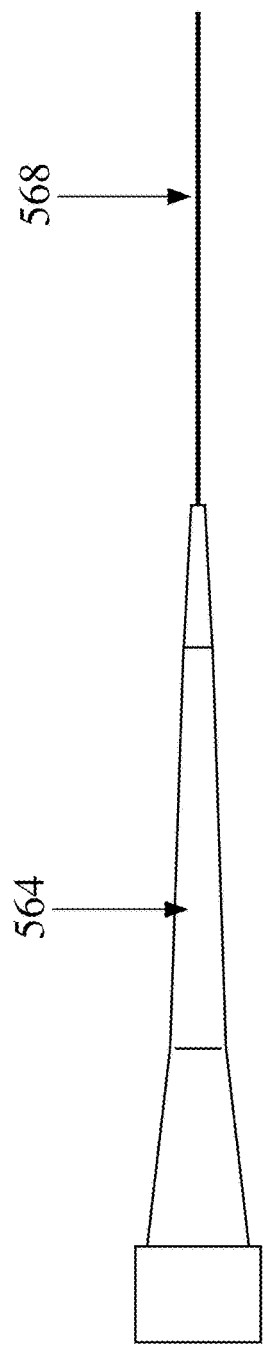

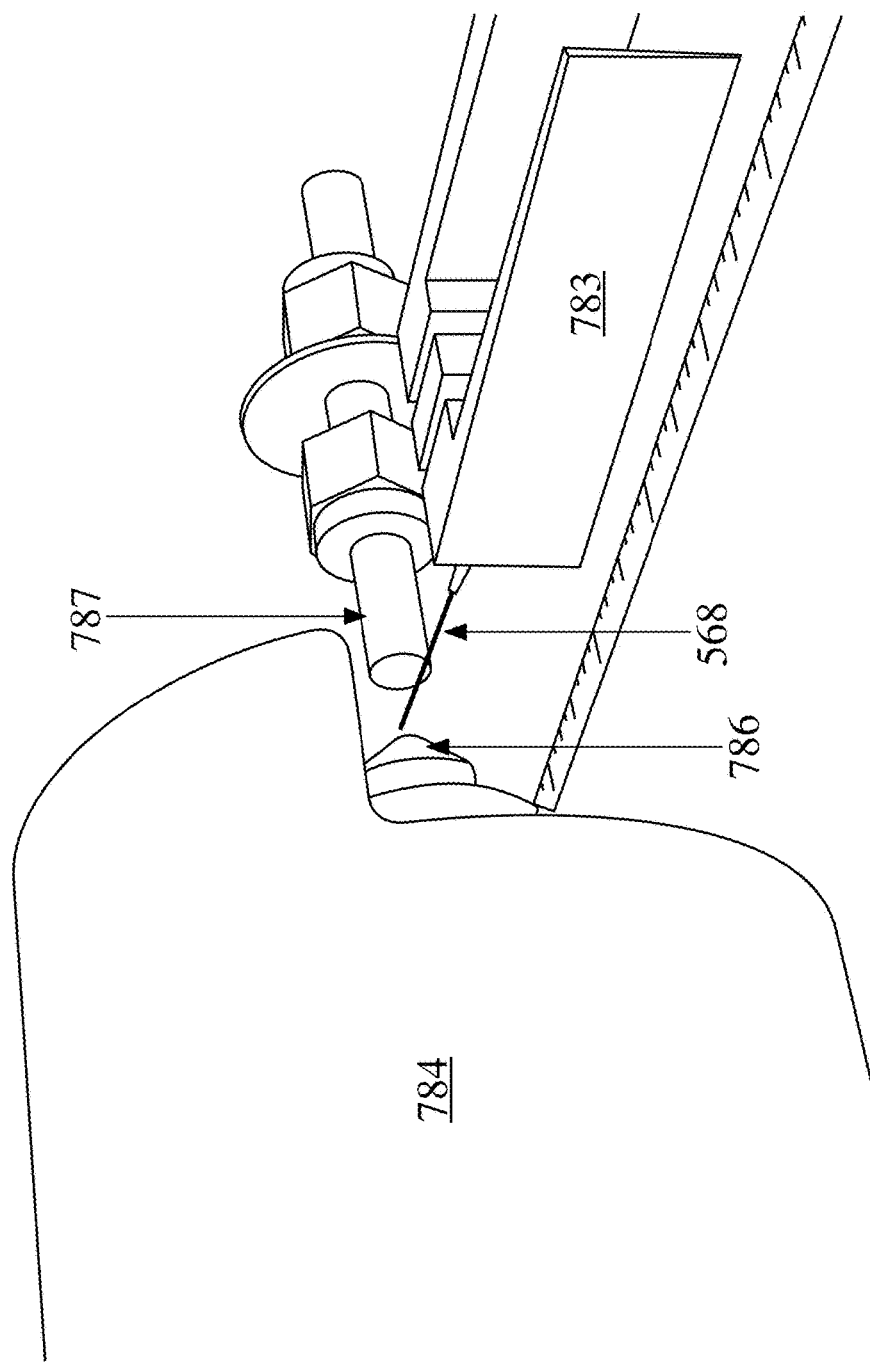

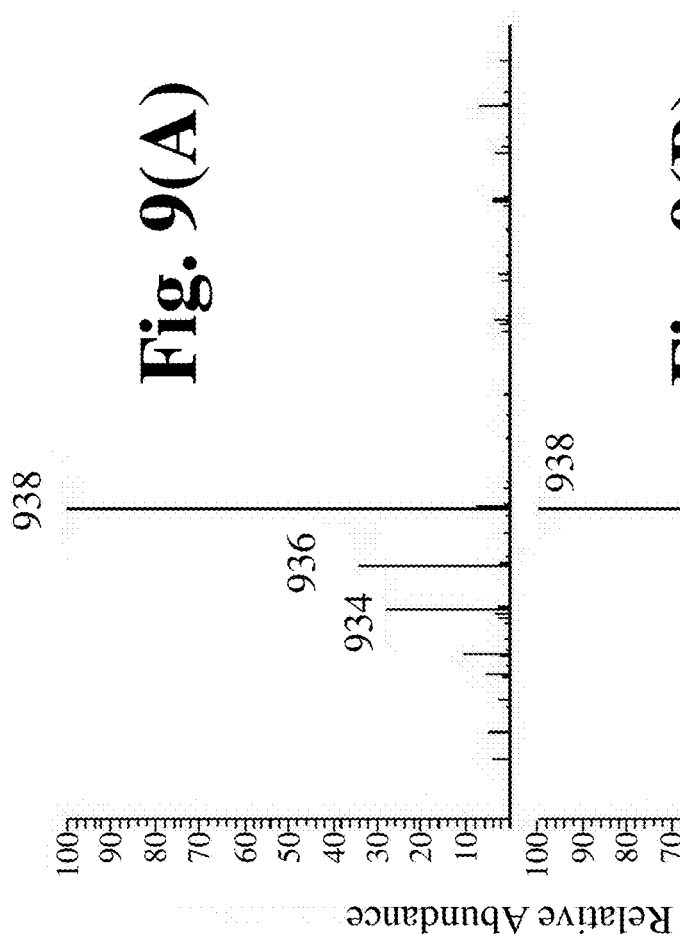

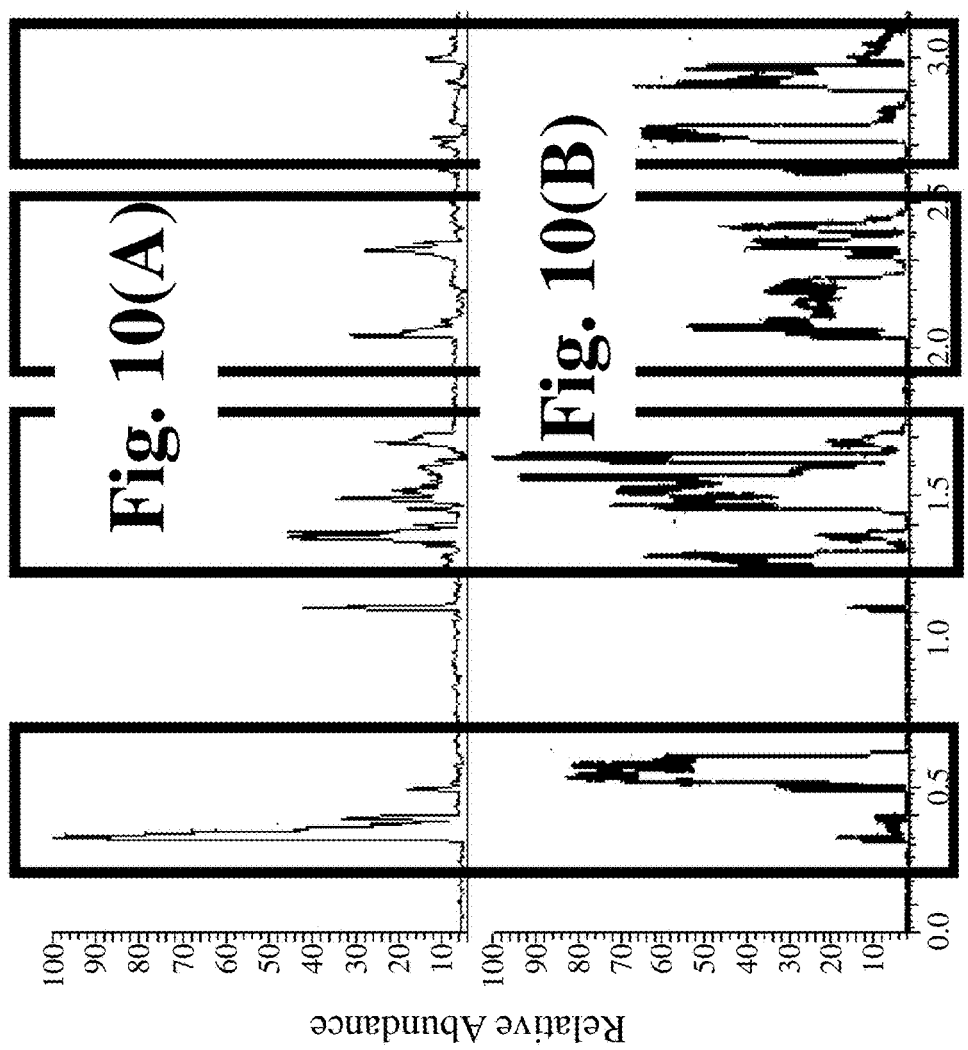

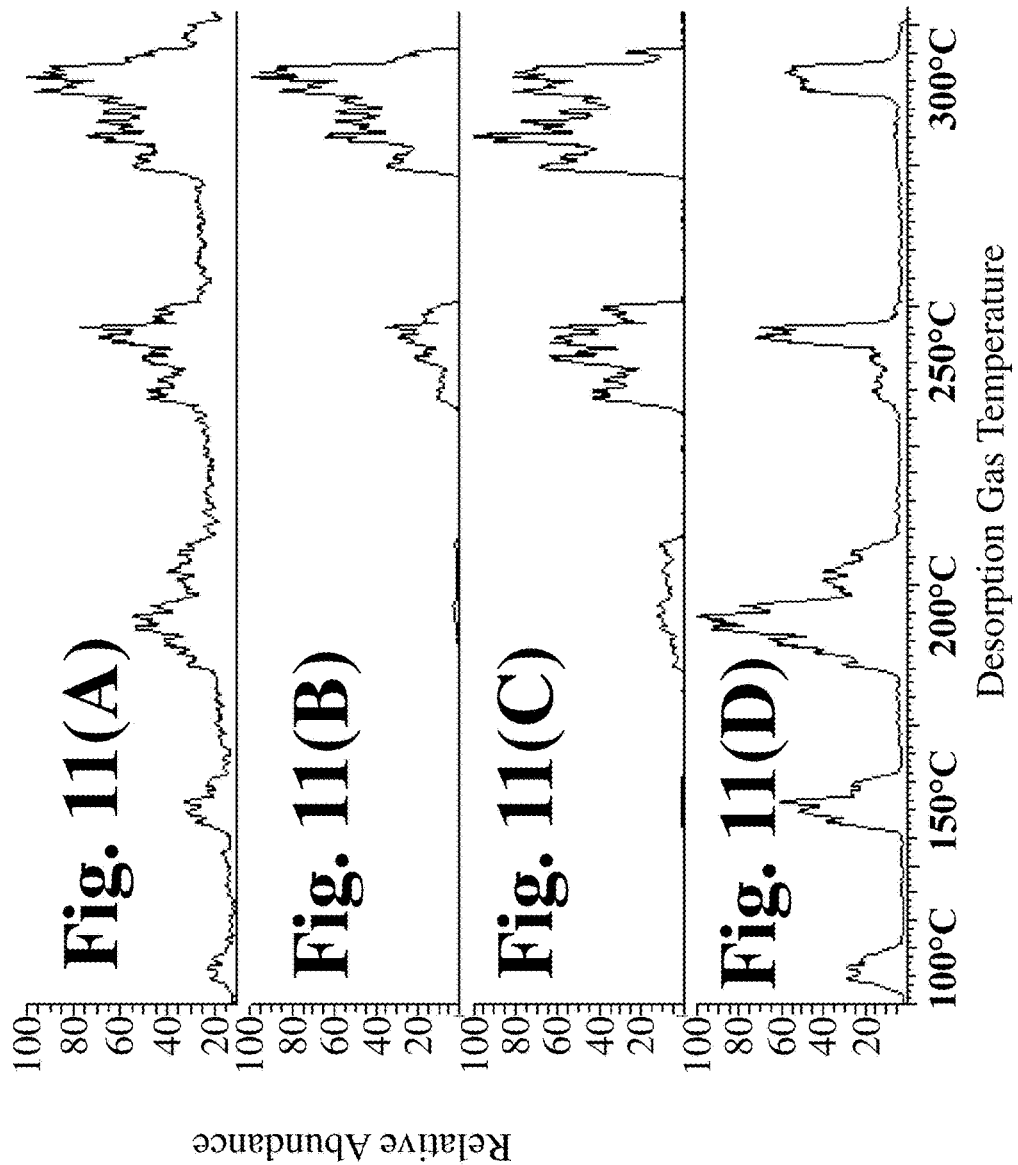

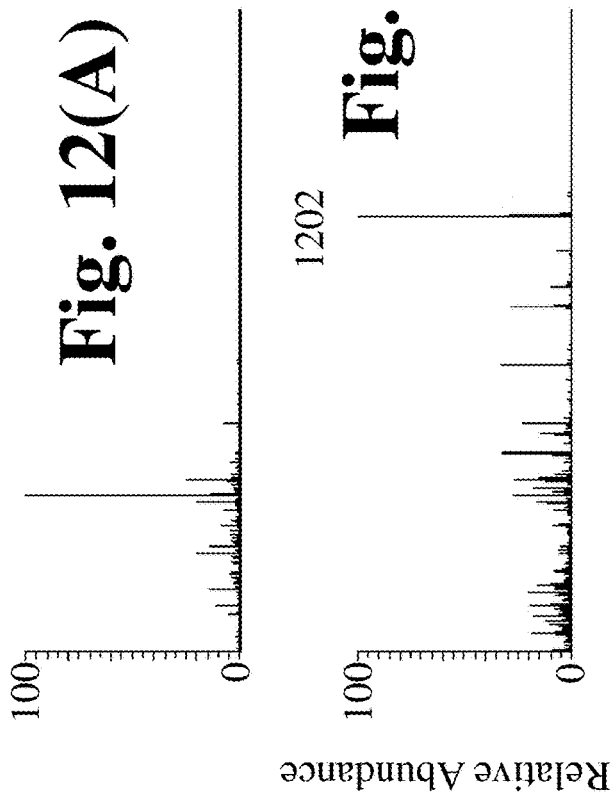

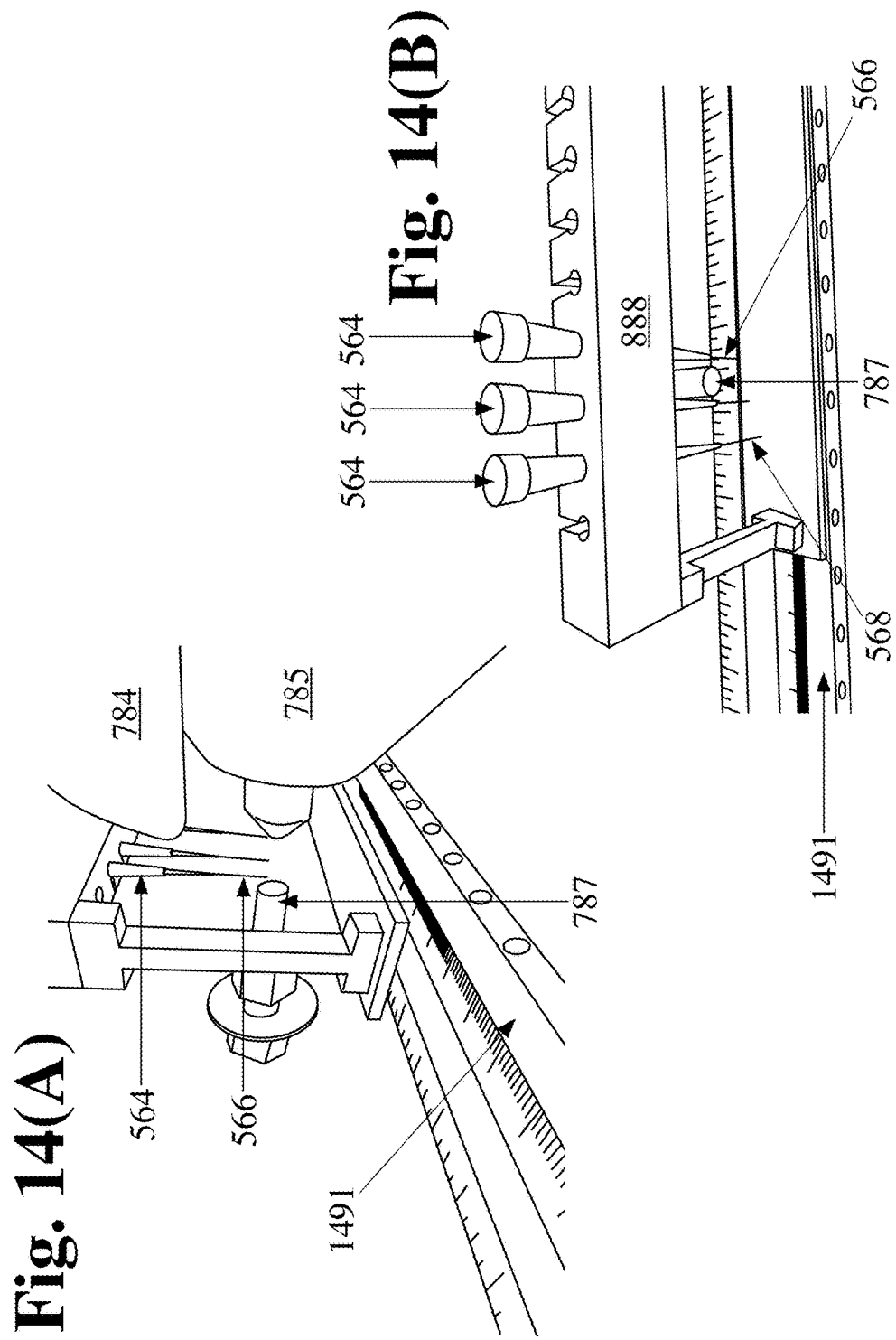

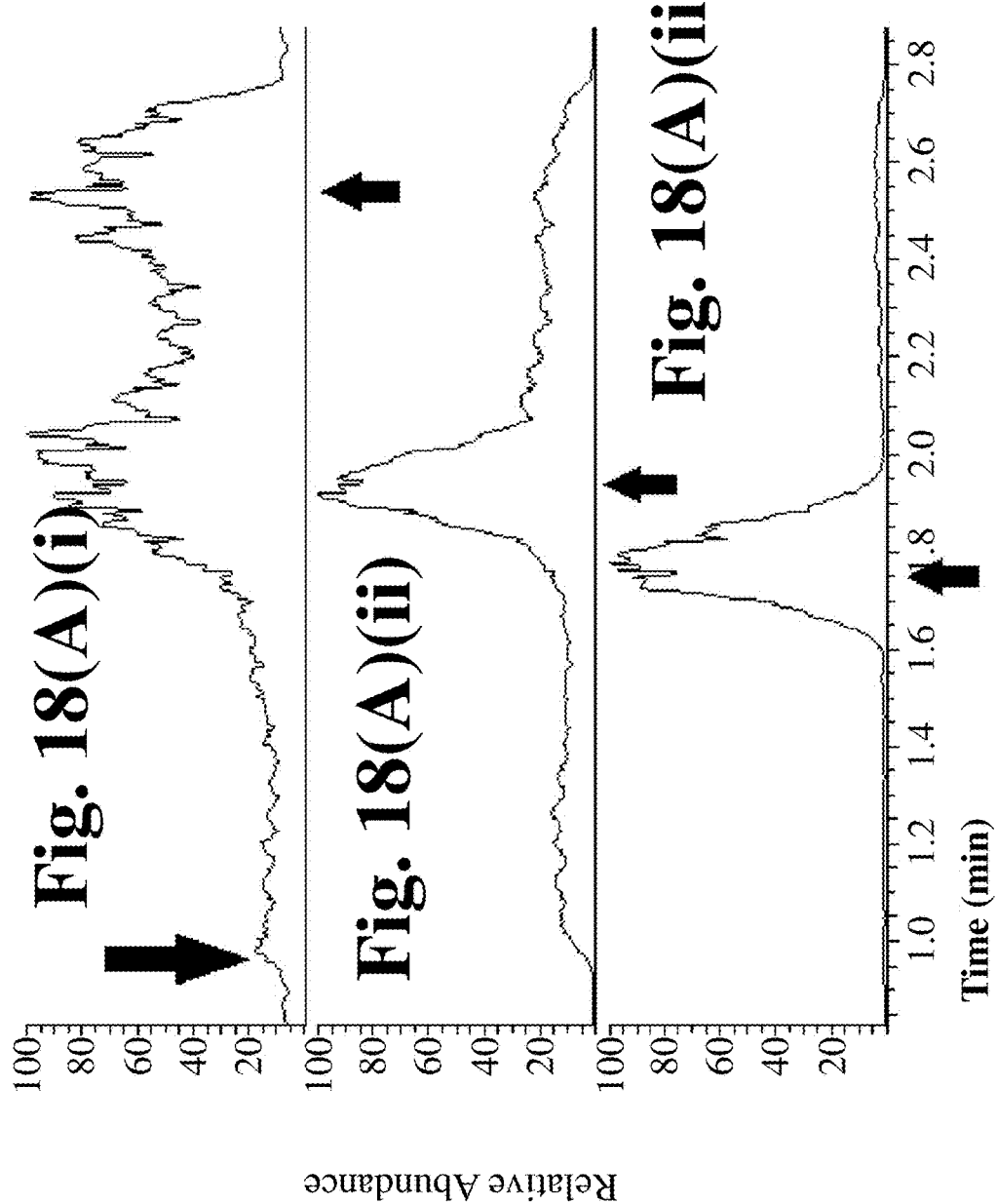

Fig. 18(B)(ii)

Fig. 18(B)(iii)

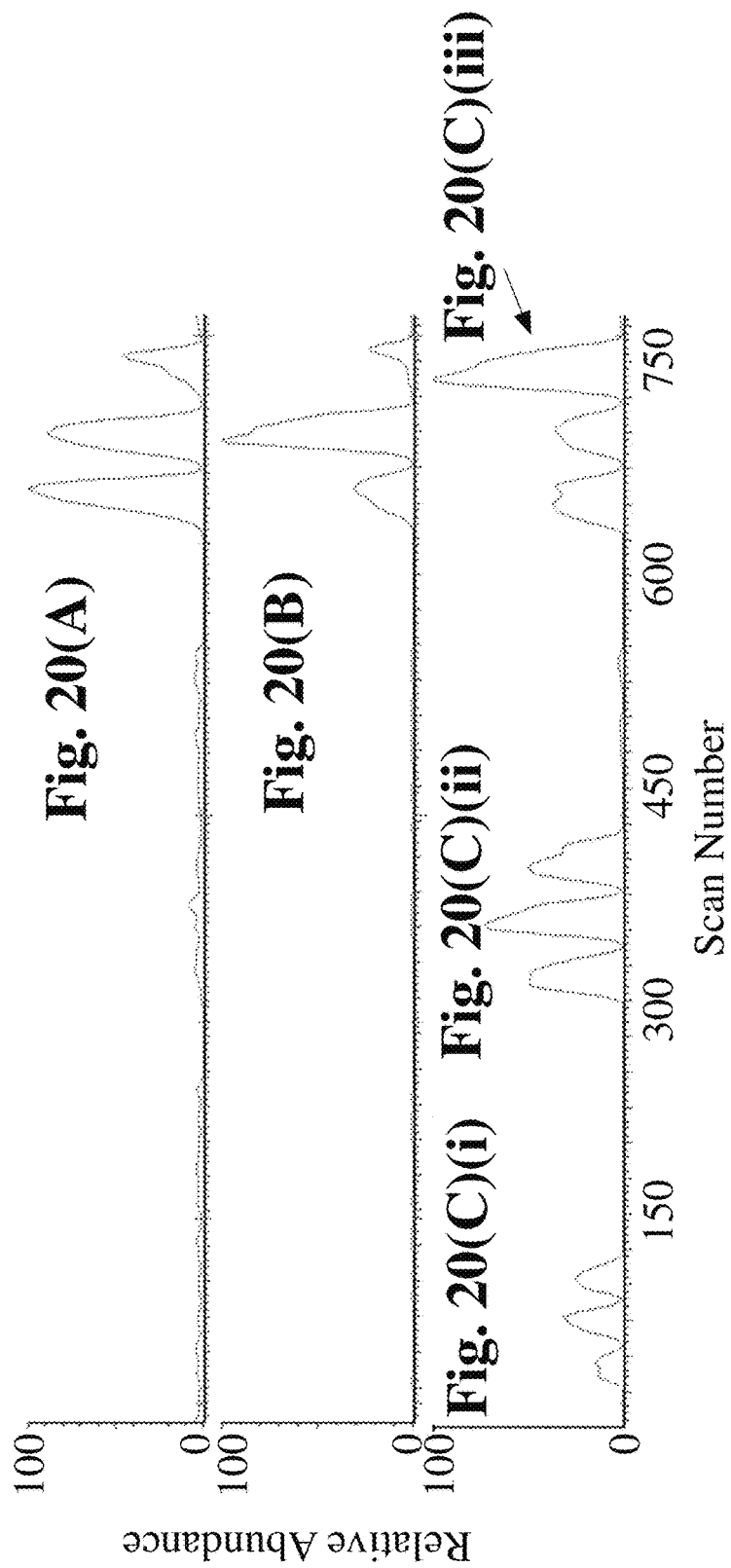

APPARATUS AND METHOD FOR RAPID CHEMICAL ANALYSIS USING DIFFERENTIAL DESORPTION

PRIORITY CLAIM

This application claims priority to (1) U.S. utility application Ser. No. 15/418,524 entitled "APPARATUS AND METHOD FOR RAPID CHEMICAL ANALYSIS USING DIFFERENTIAL DESORPTION", inventor Brian D. Musselman, filed Jan. 27, 2017, which claims priority to (2) U.S. utility application Ser. No. 15/149,161 entitled "APPARATUS AND METHOD FOR RAPID CHEMICAL ANALYSIS USING DIFFERENTIAL DESORPTION", inventor Brian D. Musselman, filed May 8, 2016, which issued as U.S. Pat. No. 9,558,926 on Jan. 31, 2017, which claims priority to (3) U.S. utility application Ser. No. 14/738,899 entitled "APPARATUS AND METHOD FOR RAPID CHEMICAL ANALYSIS USING DIFFERENTIAL DESORPTION", inventor Brian D. Musselman, filed Jun. 14, 2015, which issued as U.S. Pat. No. 9,337,007 on May 10, 2016, which claims priority to (4) U.S. Provisional Patent Application No. 62/012,417 entitled "ENSURING CONTACT TRANSFER FOR CRITICAL CHEMICAL ANALYSIS", inventor Brian D. Musselman, filed Jun. 15, 2014; and (5) U.S. Provisional Patent Application No. 62/024,880 entitled "ENSURING CONTACT TRANSFER FOR CRITICAL CHEMICAL ANALYSIS", inventor Brian D. Musselman, filed Jul. 15, 2014, the contents of each of which are incorporated herein by reference in their entireties.

FIELD OF THE INVENTION

The present invention relates to methods and devices for measuring that the contact between an object and a collector has been sufficient for measurement of chemical residues to be transferred to that collector from the object that has previously been exposed to the chemical in order to permit analysis of the chemical.

BACKGROUND OF THE INVENTION

Dr. Edmond Locard (13 Dec. 1877-4 May 1966) formulated Locard's principle which states that the perpetrator of a crime will bring something into the crime scene and leave with something from it, and that both can be used as forensic evidence. That is there is a contact transfer between the perpetrator and the crime scene. This contact transfer is the basis for much of Forensic Science. In many cases what the perpetrator brings and leaves is their fingerprint, more specifically a representation that is made up of chemicals from the perpetrator's body. The visual record of a fingerprint is frequently used by forensic chemists to identify individuals who might have been present at a crime scene.

SUMMARY OF THE INVENTION

In an embodiment of the invention, a Direct Analysis Real Time (DART) thermal profile measurement of a sample collected onto a sorbent fiber is analyzed using desorption gas heated to a plurality of different temperatures in positive ion mode. In an alternative embodiment of the invention, a DART thermal profile measurement of a sample collected onto a sorbent fiber is analyzed using desorption gas heated to a plurality of different temperatures in negative ion mode. In various embodiments of the invention, a DART thermal profile measurement of a sample that has been in contact with a single sorbent fiber can be collected by using desorption gas heated to a plurality of different temperatures. Either positive ion or negative ion or both ion mode mass spectra can be collected from the sorbent fiber in order to permit detection of a wider range of chemicals should they be present.

In an embodiment of the invention a mesh fabricated from sorbent coated wire replaces the sorbent fiber for sampling. The mesh can be made from a conductive material and can carry an electrical current. In an embodiment of the invention a sample can be deposited directly onto the mesh. A current can be applied to the mesh in order to heat the wire. Sample related molecules can be desorbed from or in close proximity to the mesh. The desorbed molecules can interact with the ionizing gas in the region between the mesh and the atmospheric pressure ionization (API)-inlet of a spectrometer. The ions that are formed from this interaction can enter the spectrometer for analysis.

BRIEF DESCRIPTION OF THE DRAWINGS

This invention is described with respect to specific embodiments thereof. Additional aspects can be appreciated from the Figures in which:

FIG. 5(A) shows a drawing of a short solid phase micro extraction (SPME) fiber (566), attached to a conventional pipette tip holder (564) to permit manipulation of the fiber according to an embodiment of the invention;

FIG. 5(B) shows a drawing of an elongated SPME fiber (568), attached to a conventional pipette tip holder (564) to permit manipulation of the fiber according to an embodiment of the invention;

FIG. 7 depicts a schematic of a SPME fiber (568) mounted on a robot positioner (783) capable of moving the fiber in and out of the ionizing volume located between the gas exit (786) of the ionizing source (784) and the inlet to the sensor (787), according to an embodiment of the invention;

FIG. 9(A) depicts a mass spectrum generated by desorption ionization of an SPME fiber with a different sorbent coating to the SPME fiber measured in FIG. 9(B) and separated by approximately nine (9) mm from the different sorbent coating to the SPME fiber measured in FIG. 9(B) in the 'Closeness Test for Matrix Effects', according to an embodiment of the invention;

FIG. 9(B) depicts a mass spectrum generated by desorption ionization of an SPME fiber with a different sorbent coating to the SPME fiber measured in FIG. 9(A) and separated by approximately nine (9) mm from the different sorbent coating to the SPME fiber measured in FIG. 9(A) in the 'Closeness Test for Matrix Effects', according to an embodiment of the invention;

FIG. 10(A) depicts the mass chromatogram for the ion detected at m/z 166 ionized from a series of SPME fibers having a mixture of C18 and Strong Cation Exchange sorbents coating positioned at decreasing distances from one another during desorption ionization in the 'Closeness Test for Matrix Effects', according to an embodiment of the invention;

FIG. 10(B) depicts the mass chromatogram for the ion detected at m/z 144 ionized from a series of multiple SPME fibers having a single sorbent C18 coating positioned at decreasing distances from one another during desorption ionization in the 'Closeness Test for Matrix Effects', according to an embodiment of the invention;

FIG. 11(A) depicts the total ion chromatogram (A) for ions of different mass values generated by exposure of a single SPME fiber with PDMS-divinyl benzene coating to ionizing gas heated to a series of increasing temperature values corresponding to those temperatures depicted on the bottom axis, according to an embodiment of the invention;

FIG. 11(B) depicts the mass chromatogram for the 443 Dalton (Da) ions generated by exposure of a single SPME fiber with PDMS-divinyl benzene coating to ionizing gas heated to a series of increasing temperature values corresponding to those temperatures depicted on the bottom axis, according to an embodiment of the invention;

FIG. 11(C) depicts the mass chromatogram for the 325 Da ions generated by exposure of a single SPME fiber with PDMS-divinyl benzene coating to ionizing gas heated to a series of increasing temperature values corresponding to those temperatures depicted on the bottom axis, according to an embodiment of the invention;

FIG. 11(D) depicts the mass chromatogram for the 223 Da ions generated by exposure of a single SPME fiber with PDMS-divinyl benzene coating to ionizing gas heated to a series of increasing temperature values corresponding to those temperatures depicted on the bottom axis, according to an embodiment of the invention;

FIG. 12(A) shows the mass spectra generated during exposure of the PDMS-divinyl benzene SPME probe to approximately 100° C., according to an embodiment of the invention;

FIG. 12(B) shows the mass spectra generated during exposure of the PDMS-divinyl benzene SPME probe to approximately 250° C., according to an embodiment of the invention;

FIG. 12(C) shows the mass spectra generated during exposure of the PDMS-divinyl benzene SPME probe to approximately 300° C., according to an embodiment of the invention;

FIG. 14(A) depicts the positioning of SPME fibers (566) mounted on a robotic sample positioner capable of positioning the individual fibers in the desorption ionization region between the gas exit (786) of the ionizing source (785) and inlet of the spectrometer (787), according to an embodiment of the invention;

FIG. 14(B) depicts a view of the position of the SPME fibers mounted on the robot module relative to the entrance of the spectroscopy system (787) with the ionizing source removed for visualization, according to an embodiment of the invention;

FIG. 18(A)(i) shows the mass chromatogram generated for m/z 123 during the desorption ionization from an elongated PDMS-divinyl benzene SPME probe after utilizing thin layer chromatography (TLC) experimental conditions to separate three components in a TLC test mixture from one another;

FIG. 18(A)(ii) shows the mass chromatogram generated for m/z 445 during the desorption ionization from an elongated PDMS-divinyl benzene SPME probe after utilizing thin layer chromatography (TLC) experimental conditions to separate three components in a TLC test mixture from one another;

FIG. 18(A)(iii) shows the mass chromatogram generated for m/z 143 during the desorption ionization from an elongated PDMS-divinyl benzene SPME probe after utilizing thin layer chromatography (TLC) experimental conditions to separate three components in a TLC test mixture from one another;

FIG. 18(B)(ii) shows the mass spectrum from the analysis of the elongated PDMS-divinyl benzene SPME probe after TLC separation of three components in TLC test mixture, where the spectrum shown was acquired at desorption times of approximately 1.95 minutes and direct desorption ionization from the fiber surface was complete by using helium gas ionized and heated to approximately 250° C., according to an embodiment of the invention;

FIG. 18(B)(iii) shows the mass spectrum from the analysis of the elongated PDMS-divinyl benzene SPME probe after TLC separation of three components in TLC test mixture, where the spectrum shown was acquired at desorption times of approximately 2.5 minutes and direct desorption ionization from the fiber surface was complete by using helium gas ionized and heated to approximately 250° C., according to an embodiment of the invention;

FIG. 19(A) shows the desorption ionization mass spectrum of a sample containing a mixture of chemicals extracted from a liquid onto a SPME fiber where the desorption gas temperature is 100° C., according to an embodiment of the invention;

FIG. 19(B) shows the desorption ionization mass spectrum of a sample containing a mixture of chemicals extracted from a liquid onto a SPME fiber where the desorption gas temperature is 200° C., according to an embodiment of the invention;

FIG. 19(C) shows the desorption ionization mass spectrum of a sample containing a mixture of chemicals extracted from a liquid onto a SPME fiber where the desorption gas temperature is 300° C., according to an embodiment of the invention;

FIG. 20(A) shows the mass chromatogram for the protonated molecule of heroin (1909) where the relative abundance increases after scan number 600 up until scan number 775 corresponding to a desorption ionization gas temperature of 300° C. according to an embodiment of the invention;

FIG. 20(B) shows the mass chromatogram for the protonated molecule of LSD (1907) where the relative abundance increases after scan number 600 up until scan number 775 corresponding to a desorption ionization gas temperature of 300° C. according to an embodiment of the invention;

FIG. 20(C)(i) shows the mass chromatogram for the protonated molecule of a pesticide, Cyanazine (1905), where the relative abundance increases after scan number 25 up to scan number 150 corresponding to a desorption ionization gas temperature of 100° C., according to an embodiment of the invention;

FIG. 20(C)(ii) shows the mass chromatogram for the protonated molecule of a pesticide, Cyanazine (1905), where the relative abundance increases after scan number 300 up until scan number 425 corresponding to a desorption ionization gas temperature of 200° C., according to an embodiment of the invention;

FIG. 20(C)(iii) shows the mass chromatogram for the protonated molecule of a pesticide, Cyanazine (1905), where the relative abundance increases after scan number 625 up until scan number 770 corresponding to a desorption ionization gas temperature of 300° C., according to an embodiment of the invention.

DETAILED DESCRIPTION OF THE INVENTION

Definitions

Figure 1:
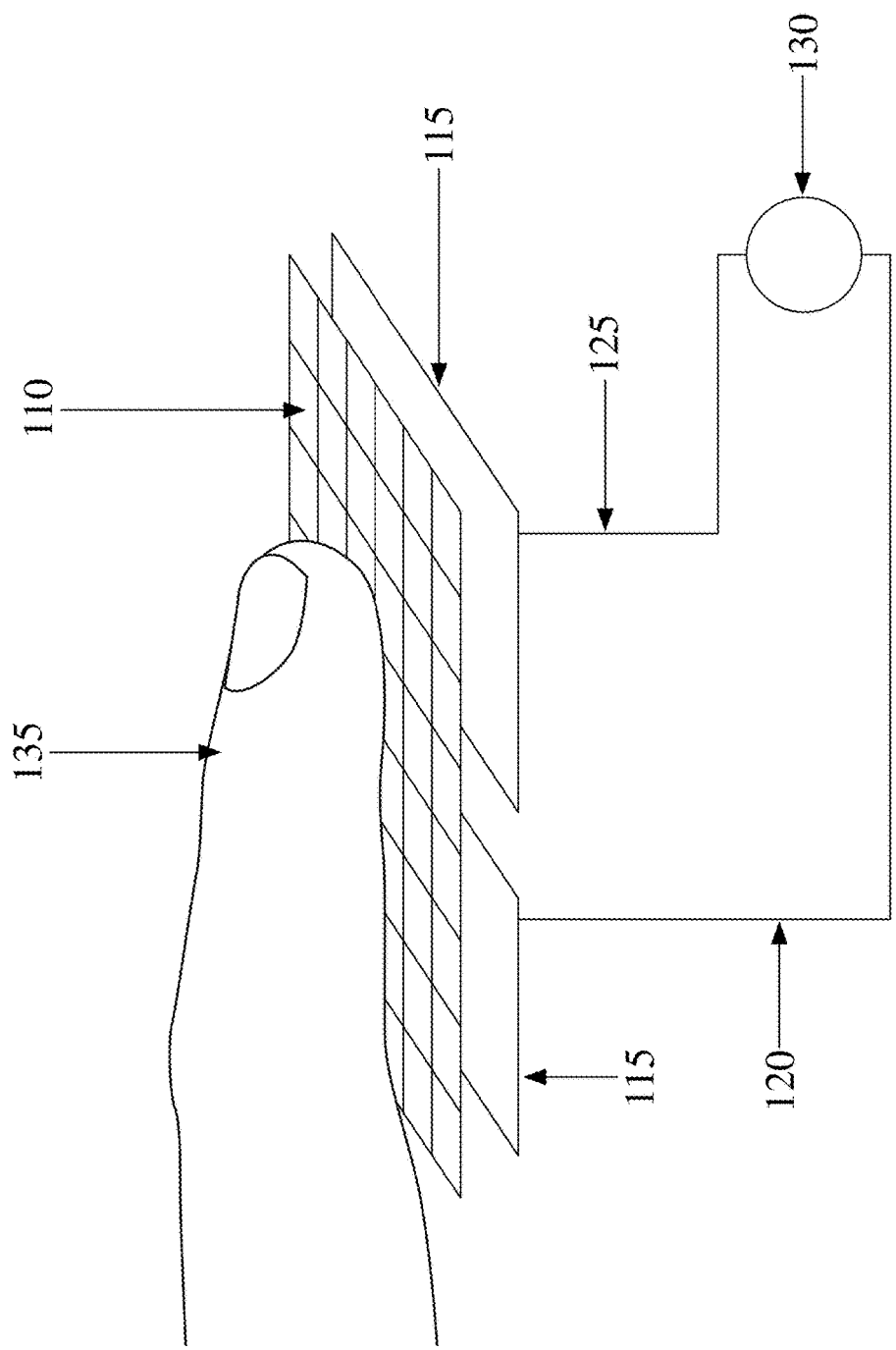
FIG. 1 depicts a schematic of a pressure sensor used to ensure that intimate contact has been made by determining the duration of contact between the finger of a subject (135) and the collector using a circuit capable of flowing current flow when the wire mesh (110) is depressed with sufficient force to complete a connection through which electrons can flow between multiple sensor components (115) the circuit wires (120, 125) and a measuring device (130), according to an embodiment of the invention.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

A vacuum of atmospheric pressure is 1 atmosphere=760 torr. Generally, 'approximately' in this pressure range encompasses a range of pressures from below $10^1$ atmosphere=$7.6 \times 10^3$ torr to $10^{-1}$ atmosphere=$7.6 \times 10^1$ torr. A vacuum of below $10^{-3}$ torr would constitute a high vacuum.

Generally, 'approximately' in this pressure range encompasses a range of pressures from below $5\times10^{-3}$ torr to $5\times10^{-6}$ torr. A vacuum of below $10^{-6}$ torr would constitute a very high vacuum. Generally, 'approximately' in this pressure range encompasses a range of pressures from below $5\times10^{-6}$ torr to $5\times10^{-9}$ torr. In the following, the phrase 'high vacuum' encompasses high vacuum and very high vacuum. The prime function of the gas ion separator is to remove the carrier gas while increasing the efficiency of transfer of neutral molecules including analyte molecules into the mass spectrometer. When constructed from non-conducting material, the gas ion separator can also be used to insulate or shield the high voltage applied to the inlet of the mass spectrometer.

A filament means one or more of a loop of wire, a segment of wire, a metal ribbon, a metal strand or an un-insulated wire, animal string, paper, perforated paper, fiber, cloth, silica, fused silica, plastic, plastic foam, polymer, Teflon, polymer impregnated Teflon, cellulose and hydrophobic support material coated and impregnated filaments. In an embodiment of the invention, a filament has a diameter of approximately 50 microns. In an alternative embodiment of the invention, a filament has a diameter of approximately 100 microns. In another alternative embodiment of the invention, a filament has a diameter of approximately 500 microns. In another embodiment of the invention, a filament has a diameter of approximately 2 mm. In measuring the diameter of a filament, approximately indicates plus or minus twenty (20) per cent. In an embodiment of the invention, the length of the filament is approximately 4 mm. In an embodiment of the invention, the length of the filament (566) in FIG. 5(A) is approximately 9 mm. In an embodiment of the invention, the length of the filament (566) in FIG. 5(B) is approximately 25 mm. In an embodiment of the invention, the length of the holder (564) in FIG. 5(B) is approximately 30 mm. In another embodiment of the invention, the length of the filament is approximately 150 mm. In measuring the length of a filament or holder, approximately indicates plus or minus twenty (20) per cent.

A metal comprises one or more elements consisting of lithium, beryllium, boron, carbon, nitrogen, oxygen, sodium, magnesium, aluminum, silicon, phosphorous, sulfur, potassium, calcium, scandium, titanium, vanadium, chromium, manganese, iron, cobalt, nickel, copper, zinc, gallium, germanium, arsenic, selenium, rubidium, strontium, yttrium, zirconium, niobium, molybdenum, technetium, ruthenium, rhodium, palladium, silver, cadmium, indium, tin, antimony, tellurium, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, thallium, lead, bismuth, polonium, francium and radium. Thus a metal includes for example, a nickel titanium alloy known as nitinol or a chromium iron alloy used to make stainless steel.

A plastic comprises one or more of polystyrene, high impact polystyrene, polypropylene, polycarbonate, low density polyethylene, high density polyethylene, polypropylene, acrylonitrile butadiene styrene, polyphenyl ether alloyed with high impact polystyrene, expanded polystyrene, polyphenylene ether and polystyrene impregnated with pentane, a blend of polyphenylene ether and polystyrene impregnated with pentane or polyethylene and polypropylene.

A polymer comprises a material synthesized from one or more reagents selected from the group comprising of styrene, propylene, carbonate, ethylene, acrylonitrile, butadiene, vinyl chloride, vinyl fluoride, ethylene terephthalate, dimethyl terephthalate, bis-beta-terephthalate, naphthalene dicarboxylic acid, 4-hydroxybenzoic acid, 6-hyderoxynaphthalene-2-carboxylic acid, mono ethylene glycol (1,2 ethanediol), cyclohexylene-dimethanol, 1,4-butanediol, 1,3-butanediol, polyester, cyclohexane dimethanol, terephthalic acid, isophthalic acid, methylamine, ethylamine, ethanolamine, dimethylamine, hexamthylamine diamine (hexane-1,6-diamine), pentamethylene diamine, methylethanolamine, trimethylamine, aziridine, piperidine, N-methylpiperideine, anhydrous formaldehyde, phenol, bisphenol A, cyclohexanone, trioxane, dioxolane, ethylene oxide, adipoyl chloride, adipic, adipic acid (hexanedioic acid), sebacic acid, glycolic acid, lactide, caprolactone, aminocaproic acid and or a blend of two or more materials synthesized from the polymerization of these reagents.

A plastic foam is a polymer or plastic in which a gaseous bubble is trapped including polyurethane, expanded polystyrene, phenolic foam, XPS foam and quantum foam.

A mesh means one or more of two or more connected filaments, two or more connected strings, foam, a grid, perforated paper, screens, paper screens, plastic screens, fiber screens, cloth screens, polymer screens, silica screens, Teflon screens, polymer impregnated Teflon screens, cellulose screens and hydrophobic support material coated or impregnated mesh. In various embodiments of the invention, a mesh includes one or more of three or more connected filaments, three or more connected strings, mesh, foam, a grid, perforated paper, screens, plastic screens, fiber screens, cloth, and polymer screens. In an embodiment of the invention, a mesh can have approximately 10 filaments per cm. In an alternative embodiment of the invention, a mesh can have approximately 100 filaments per cm. In designing the number of filaments per cm, approximately indicates plus or minus twenty (20) per cent.

Deployed means attached, affixed, adhered, inserted, or otherwise associated. Thus a paper screen can be deployed on a card where the paper for the screen and the paper for the card are of a unitary construction. A card means a sample holder. A card can be made of one or more of paper, cardboard, insulating materials, conductive materials, plastic, polymers, minerals and metals. A mesh can be inserted and held in a card. A mesh can be clamped in a card. Alternatively, a metal mesh can be welded into a metal card. A reservoir is a vessel used to contain one or more of a liquid, a gaseous or a solid sample.

A sorbent fiber means a solid surface which has been coated with a thin chemical film that is capable of retaining certain chemical entities by interacting with them forming either a non-covalent or in some cases a covalent bond between the chemicals on the surface and the chemicals in the surrounding environment. In practice the thin film is greater than approximately 10 microns and less than approximately 500 microns in thickness. In designing the thickness of the film, approximately indicates plus or minus twenty (20) per cent.

A desorption ionization source includes DART, DESI, a MALDI source, a UV laser, an IR laser, atmospheric pressure chemical ionization (APCI) spray, directed electrospray, electrospray, a dielectric barrier discharge, and a flowing after-glow plasma source.

In the following description, various aspects of the present invention will be described. However, it will be apparent to those skilled in the art that the present invention can be practiced with only some or all aspects of the present invention. For purposes of explanation, specific numbers, materials, and configurations are set forth in order to provide a thorough understanding of the present invention. However, it will be apparent to one skilled in the art that the present invention can be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

The unique characteristics that define a fingerprint image are in reality chemicals excreted through the skin that have been visualized by using dyes that interact with those chemicals. Due in part to the difficulty of preparing samples, the actual chemicals in the fingerprints derived from objects that the suspect touched, ingested, took as a medication or was otherwise exposed to, are not generally recognized as being identifiers that the suspect was present at a crime scene. Those chemicals may include drug metabolites, narcotics, explosive residues and foodstuffs that the suspect has come into contact with prior to the event of forensic interest.

In practice, everyday thousands of chemical analyses of human subjects are carried out to determine compliance with a drug treatment program, presence/absence of an illegal drug or in the medical setting to diagnose a disease. The medical community also examines the metabolites present in young children for signs of inherited diseases on a routine basis.

Sample collection is relatively straight forward. In the case of buccal or urine samples there is sufficient volume to conduct chemical analysis using a variety of chemical analysis instruments. In contrast to buccal, or urine samples the collection of chemicals from fingerprints for analysis not a routine matter. Although uncommon, there are reports in which the chemicals present in a fingerprint have been imaged using ambient ionization mass spectrometry. Indeed, the use of the DART ambient ionization method for detection of metabolites of drugs directly from fingerprints on a glass surface was documented in the first publication describing the method.

Solid phase extraction methods facilitate rapid isolation of target compounds from common chemicals that together make up a sample of interest. Solid phase extraction technologies have evolved to the point where a wide array of devices is available for an analytical chemist to use with different types of samples. For example, the development of thin film solid phase extraction coatings bound to fibers, so called solid phase micro extraction (SPME), has enabled the detection of trace quantities of specific targeted molecules for determination of environmental toxins in water, pesticides in foods and beverages, and metabolites in urine and blood to name a few application. SPME materials can be optimized for use with different target compounds by changing the chemical composition of the sorbent material. Traditionally SPME derived samples are analyzed by using instrumentation including gas chromatography (GC), GC/mass spectrometry (MS) (GCMS), liquid chromatography (LC) and LCMS.

Figure 15:
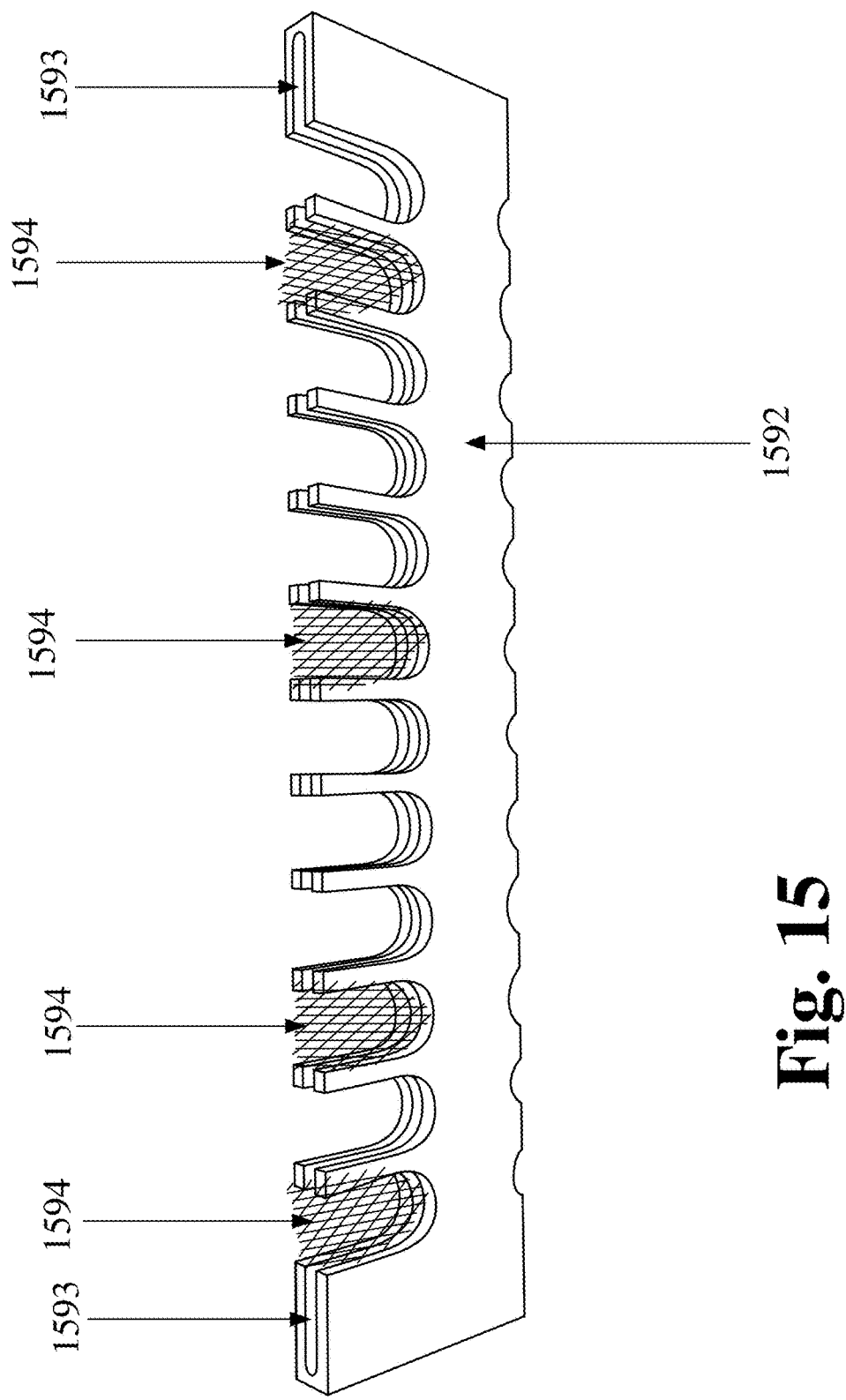
FIG. 15 shows a schematic of a robotic module (1592) holding pieces of sorbent coated wire (1594) for analysis, according to an embodiment of the invention.

GC, GCMS, LC and LCMS instruments are capable of sampling a single fiber one at a time. Development of devices for desorption ionization of molecules direct from solids, and liquids in open air using a DART source has previously been described in U.S. Pat. No. 6,949,741 "Atmospheric Pressure Ionization Source" which is herein expressly incorporated by reference in its entirety. DART uses a heated carrier gas to effect desorption of sample into that same carrier gas where gas phase ionization occurs. A gas ion separator described in U.S. Pat. No. 7,700,913, "Sampling system for use with surface ionization spectroscopy" which is herein expressly incorporated by reference in its entirety can be used to improve the efficiency of sampling with DART. The DART method enabled direct desorption of SPME in different formats such as screens in open air which has led to new methods of analysis. FIG. 15 shows a schematic of sorbent coated screens (1594) mounted in the groove (1593) of a robotic sample presentation module (1592) for analysis, according to an embodiment of the invention.

In security applications chemical residues are sampled from the hand, fingers, clothing, suitcase surfaces and other locations by using cloth swabs or plastic tickets. Sampling is carried out by a person following a protocol that in most cases involves using a wand device that permits collection of the sample without the person collecting the sample having to touch the cloth or plastic ticket being used to sample the subject. The inspector is trained to ensure that a proper sample has been acquired by applying sufficient force to the wand so that it makes intimate contact with the subject or surface being tested as called for in the sampling protocol. In an embodiment of the invention a wire mesh collector is used as a fingerprint collector. The surface of the wire mesh is coated with sorbent or sorbents capable of retaining chemicals applied to it. The force between the object being sampled and the wire mesh or other sampling device must be sufficient to ensure transfer of the chemical signature, which will be described as 'intimate contact'.

Figure 2:
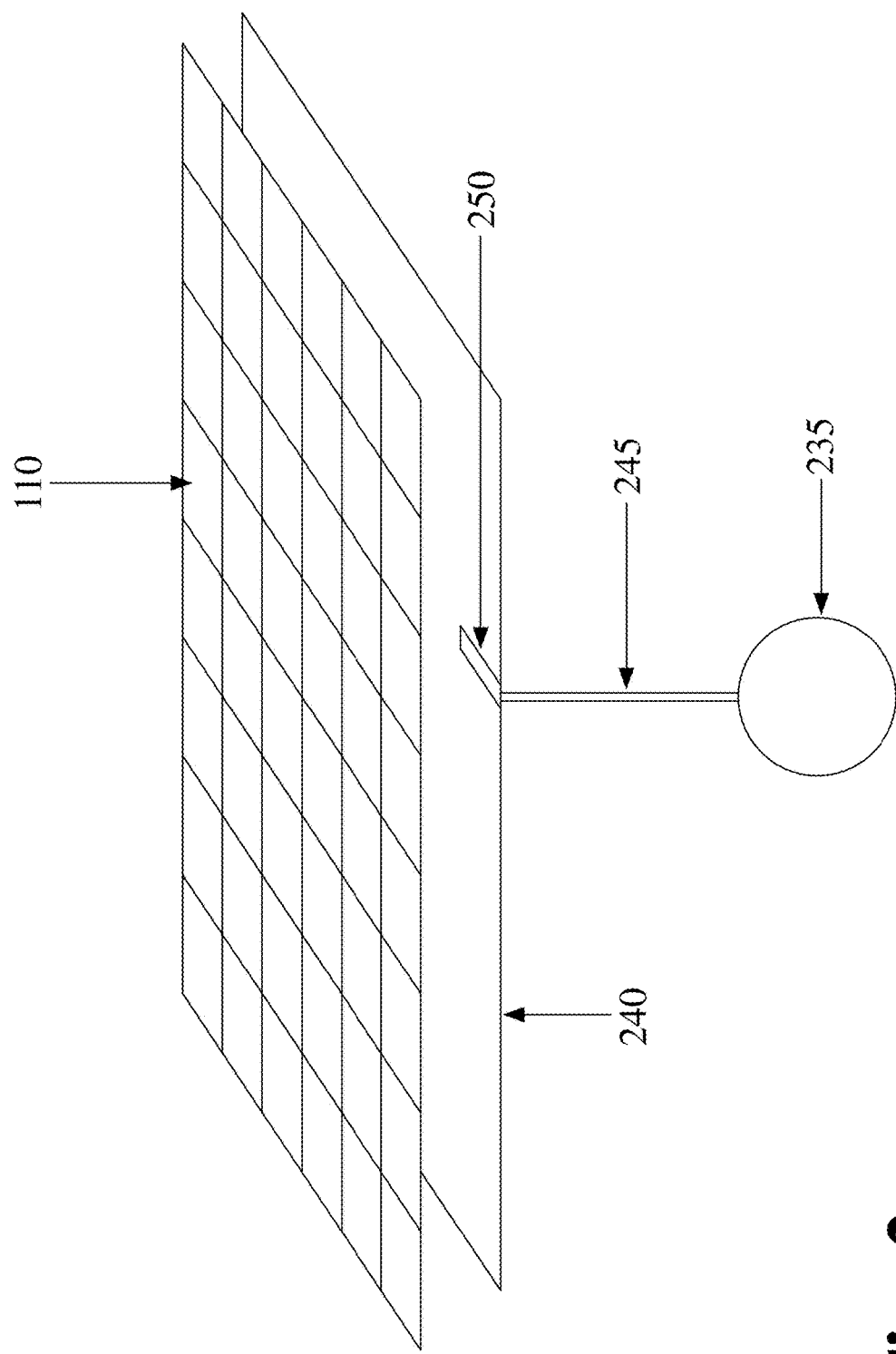
FIG. 2 depicts a schematic of a temperature sensor used to ensure that intimate contact has been made between the wire mesh (110) and the subject (not shown) by measuring the temperature of the wire mesh or measuring the change in temperature of a sensor surface (240) to which a thermocouple (250) may be attached with electrodes or wires (245) connecting the thermocouple to its controller (235) as the wire mesh (110) is pushed down to contact that sensor surface.
Figure 3:
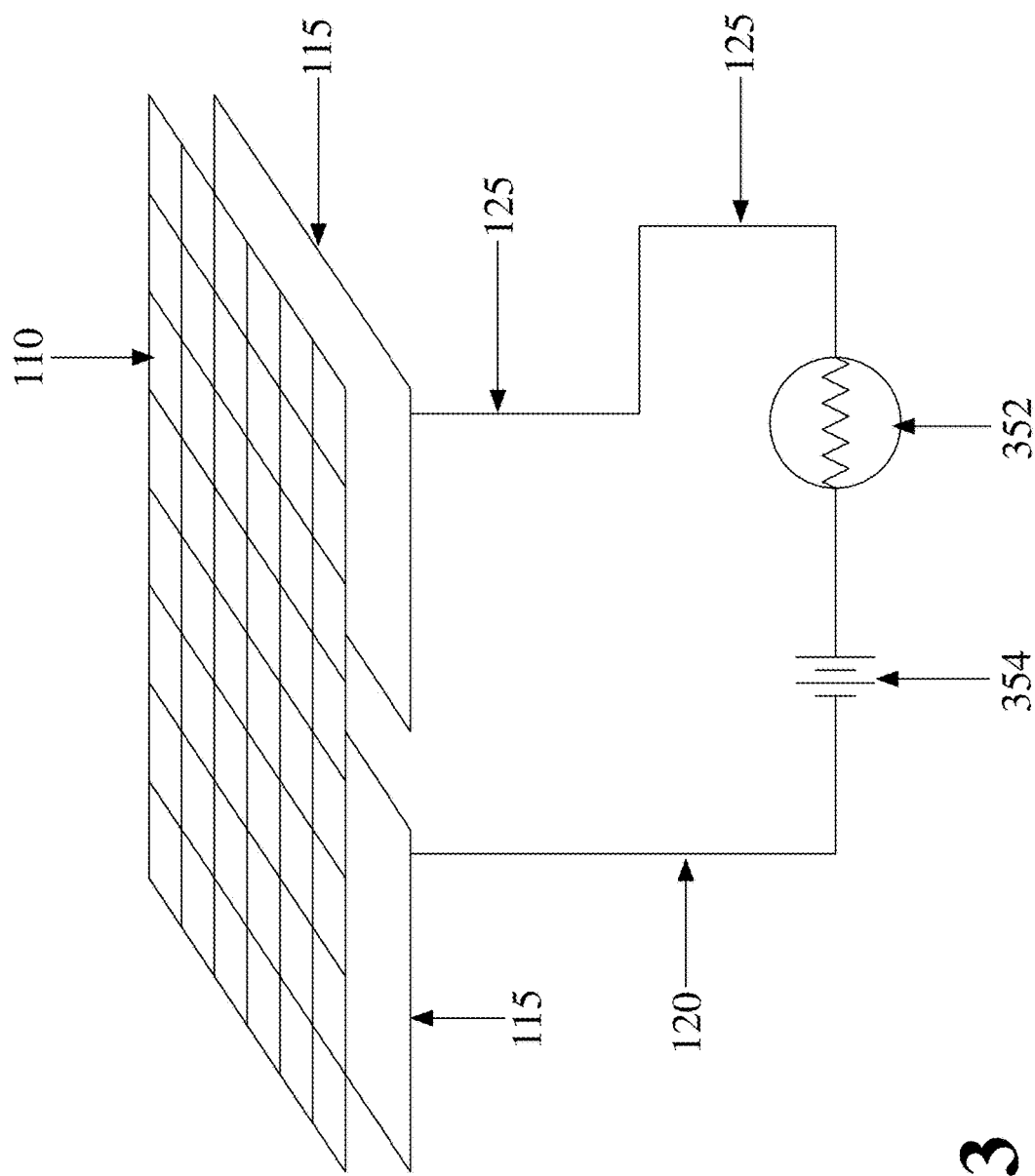
FIG. 3 depicts a schematic of an circuit containing a conductivity sensor (352) used to ensure that intimate contact has been made by measuring the conductivity change through the circuit connected to the wire mesh (110) by using wires (120, 125) where the circuit is completed when the wire mesh is depressed by pressing the sample (135) against the wire mesh (110) so that it touches both sensor components (115) closing the circuit which contains the sensor (352) to which a voltage may or may not be applied by using a power supply (354). The change in conductivity being used in order to determine the duration of contact, according to an embodiment of the invention.
Figure 4A:
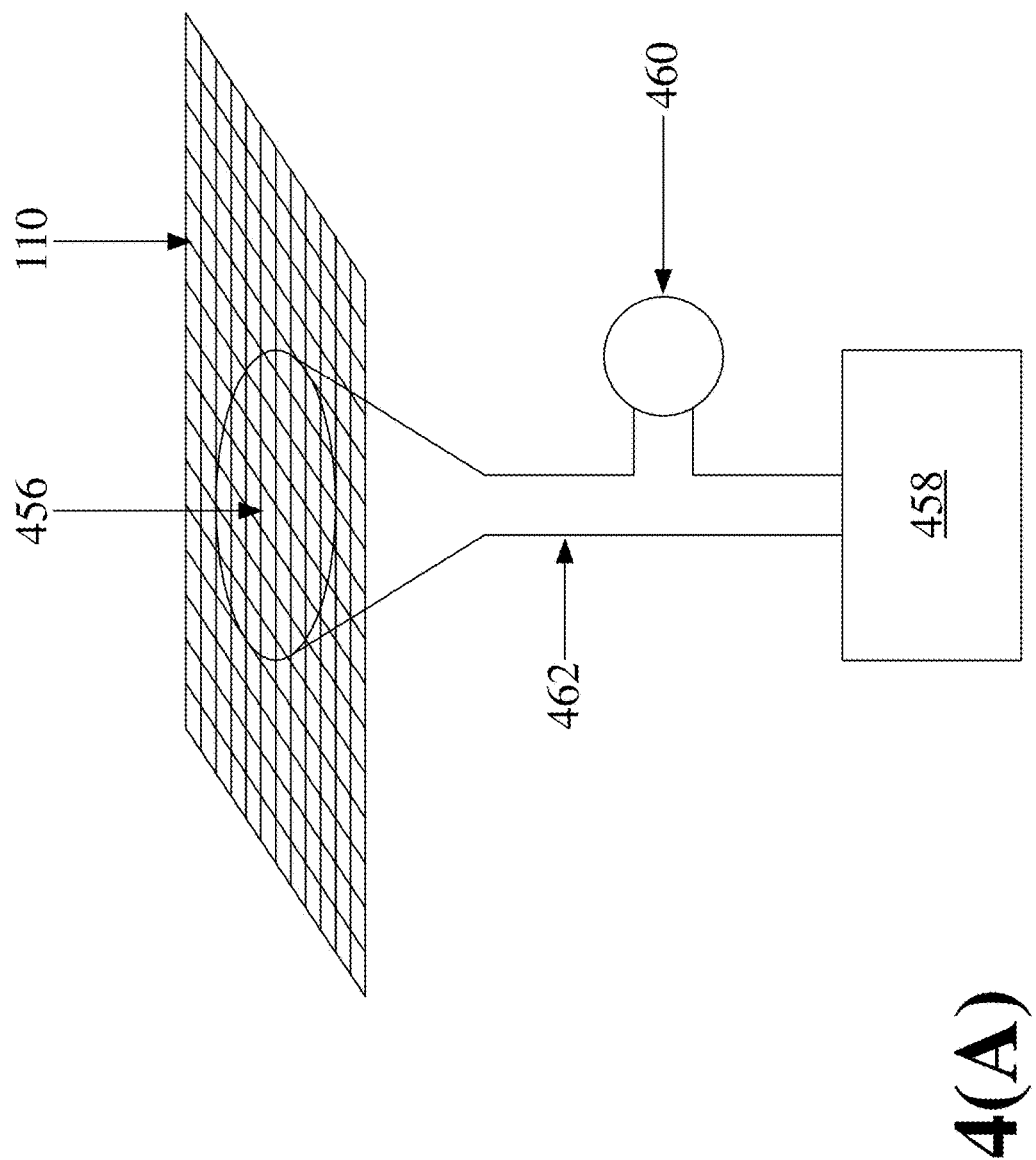
FIG. 4(A) depicts a schematic of an pressure sensor (460) used to ensure that intimate contact has been made by measuring the pressure under the wire mesh (110) screen or the change in the air pressure under the wire mesh after it is depressed against the inlet opening (456) of a volume (462) to which a pressure generator (458) is attached to produce an increase in pressure as the opening of the volume is covered by the sample (not shown) in order to determine the duration of contact, according to an embodiment of the invention.
Figure 4B:
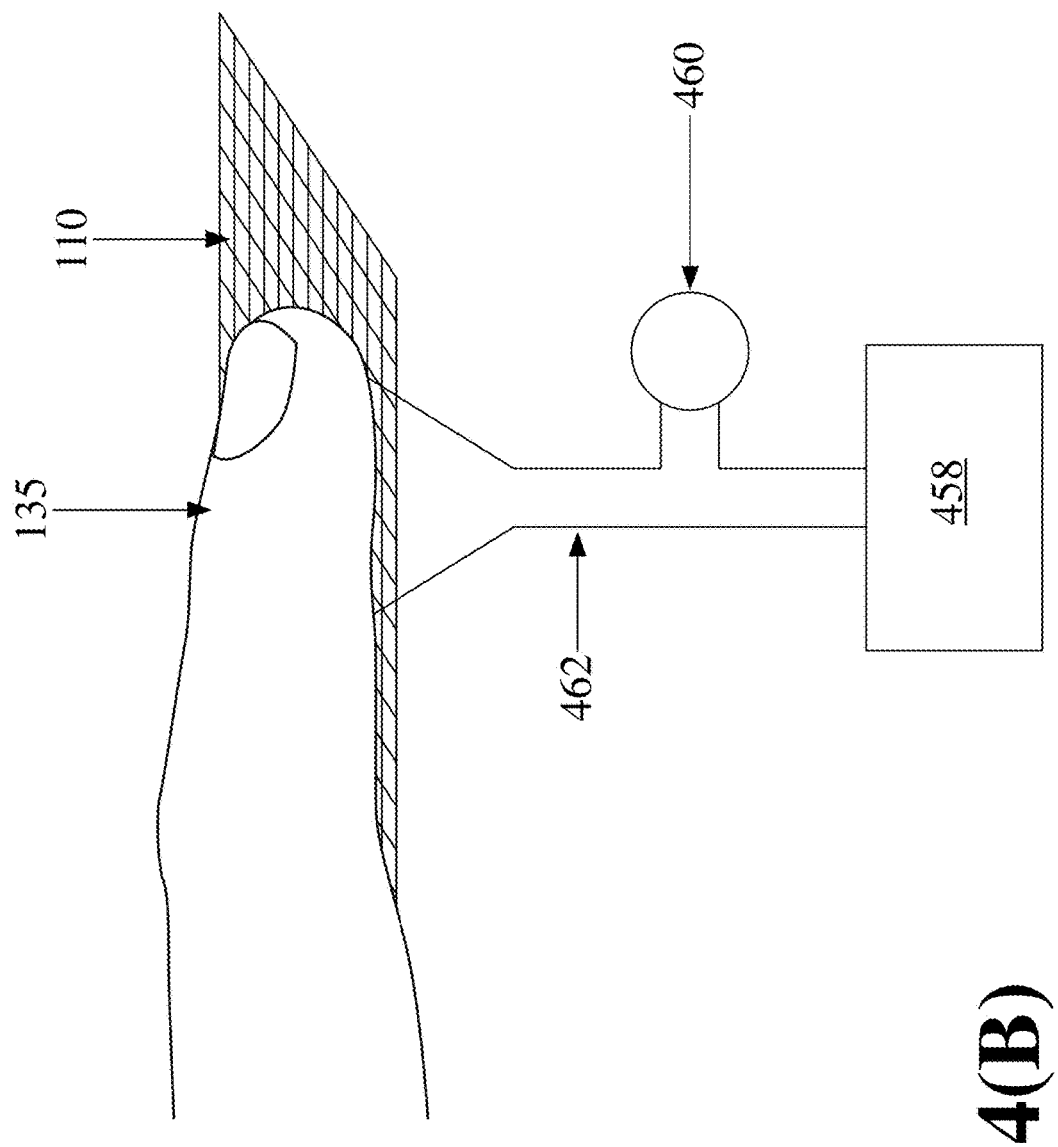
FIG. 4(B) depicts a schematic of a finger (135) as the subject covering both the wire mesh (110) and opening of the volume (462) of the device shown in FIG. 4(A) as the finger is pressed against the wire mesh blocking flow of gas into the volume (462) below the wire mesh. The low pressure vacuum pump (458) is utilized to reduce the pressure in the enclosed volume. The vacuum in the volume is measured by the sensor (460) according to an embodiment of the invention.

In an embodiment of the invention in order to ensure that intimate contact has been made a sensor is used to determine the duration of contact between the subject and the collector by using a circuit that is capable of having current flow through the circuit when the wire mesh is depressed with sufficient force to complete the circuit as shown in FIG. 1. In an alternative embodiment of the invention in order to ensure that intimate contact has been made a sensor may measure the temperature of the wire mesh or measure the change in temperature of the wire mesh in order to determine the duration of contact as shown in FIG. 2. The sensor surface (240) temperature is determined by converting the signal from the thermocouple (250) in contact with the sensor surface (240) where current flowing through components (245 and 235) results in an electrical current determined by the measurement device (235). The device described is use in order to determine the duration of contact, according to an embodiment of the invention. In another alternative embodiment of the invention, in order to ensure that intimate contact has been made a sensor may measure the conductivity of the wire mesh or changes in the conductivity through the wire mesh in order to determine the duration of contact, as shown in FIG. 3. In a further alternative embodiment of the invention, in order to ensure that intimate contact has been made a sensor may measure the air pressure under the wire mesh screen or change in the air pressure under the wire mesh in order to determine the duration of contact. In another embodiment of the invention in order to ensure that intimate contact has been made a sensor may measure the vacuum in a chamber under the wire mesh screen or change in the vacuum in a chamber under the wire mesh in order to determine the duration of contact, as shown in FIG. 4. In an embodiment of the invention, the sensor output is connected to a device that provides a signal indicating that the duration and force of the contact has been sufficient for completion of sample collection.

Exposure to dangerous chemical by breathing or by contact can therefore lead to some of those materials appearing in the fingerprint mixed with the lipids that exit the skin. The identity of those materials might be determined with a viable sampling method and the proper detection system.

DART analysis of fingerprint chemicals from surfaces has been reporting using the DART ambient ionization method. Subsequently other ambient ionization methods have been utilized including desorption electrospray ionization which was used to permit detection of individual specks of a gunshot residue dispersed throughout the fingerprint of an individual reported to have fired a weapon shortly before acquisition of the data. DART has been used to detect drug and drug metabolites from a prescription drug taken orally. Practically speaking the detection of explosives and other chemicals using ion mobility spectrometry is common practice in airport and other secure settings. This is also a form of chemical fingerprint detection.

In an embodiment of the invention direct sampling of the chemicals present on the surface of a finger has been accomplished by first having the subject make contact with a sorbent coated surface. The surface was subsequently analyzed in seconds by using an ambient ionization direct analysis in real time (DART) mass spectrometry device without extraction of the surface that had been touched by the finger. Ions detected in the mass spectrum are used to determine that the individual from which the sample was acquired had come into contact with those chemicals in the recent past or had come into contact with another individual who had been exposed to that chemical.

The desorption ionization region is located between the DART source exit and the atmospheric pressure inlet of the detection system.

There remain encumbrances to the employment of the DART technique for a variety of samples and various experimental conditions. A schematic representation of two different SPME fibers is shown in FIG. 5. In order to permit manipulation of the fiber by either hand or robotic means the fiber is mounted to a holder, in this case a plastic pipette tip (564) which has been heated and compressed to surround and bind the proximal end of the fiber. FIG. 5(A) shows a drawing of a short solid phase micro extraction (SPME) fiber (566), the proximal end of which is molded into the distal end of a plastic pipette tip (564) according to an embodiment of the invention. FIG. 5(B) shows a drawing of an elongated SPME fiber (568), also molded into the distal end of a plastic pipette tip, according to an embodiment of the invention. With SPME the capture and retention of compounds of interest is carried out by the chemicals present in the sorbent coating binding to the fiber surface. The sorbent of each fiber is capable of binding chemicals based on the functional groups that are present in the molecule while excluding binding of molecules that do not have the functional groups that the sorbent can bind. Extraction occurs when the fiber comes into contact with either a gas or liquid containing those molecules with appropriate functional groups and thereby affinity to be chemically bound to the sorbent. Sampling can be made either from a sample constrained by an enclosure or directly from the surrounding environment. These easy-to-use sampling methods have facilitated development of numerous devices suitable for sampling chemicals in the field.

Figure 6A:
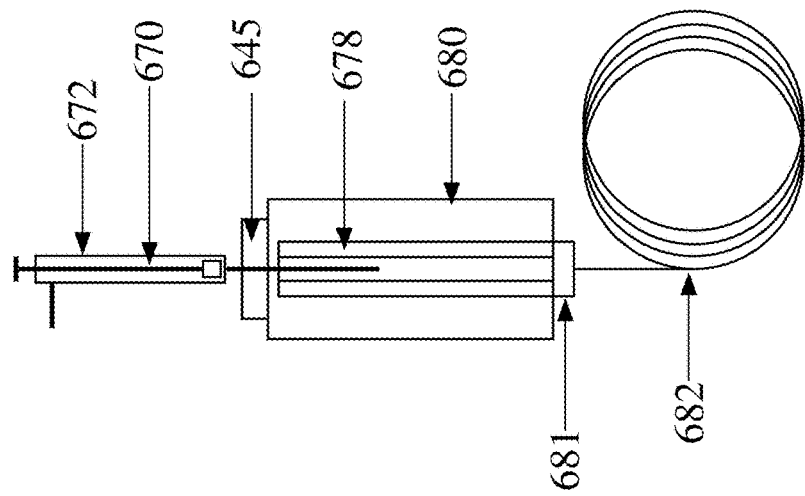
FIG. 6(A) shows a prior art syringe aligned with the septum of a vial.
Figure 6B:
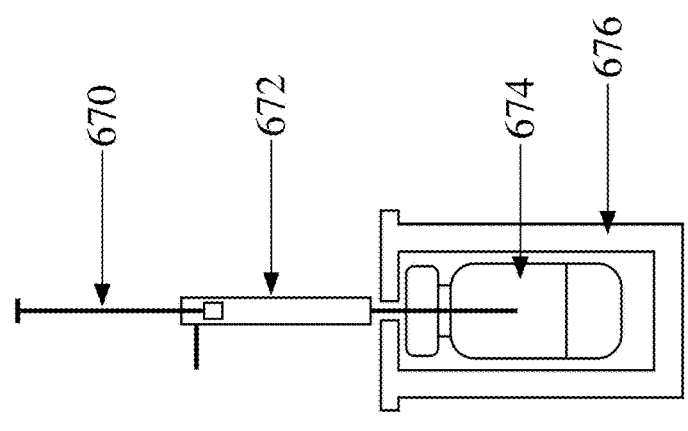
FIG. 6(B) shows the prior art syringe of FIG. 6(A) inserted into the septum of a vial.
Figure 6C:
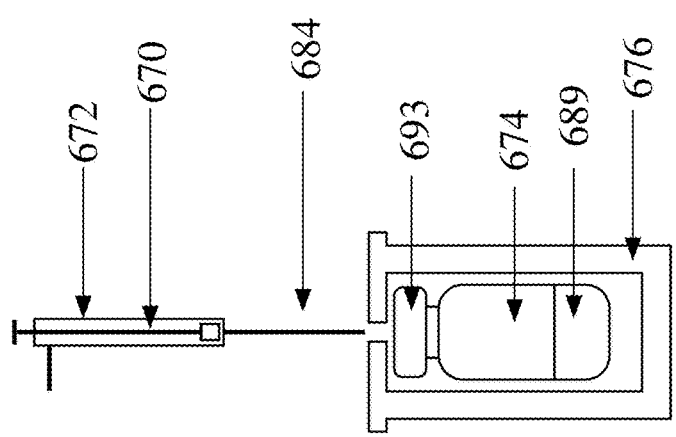
FIG. 6(C) shows a prior art GC injector being loaded with the syringe of FIG. 6A.

When sampling liquids using SPME, the first step of the analysis is to immerse the sorbent coated fiber into the liquid. The analysis can be improved by either moving the fiber itself or the container holding the sample and the fiber. This movement facilitates interaction between the chemicals in the sample and the sorbent on the fiber. The critical second step of the analytical process is the transfer of compounds trapped on the sorbent coated fiber to an instrument for the analysis to occur. This step typically involves inserting the fiber into a single enclosed region to effect thermal desorption of the target compounds into the gas phase for gas chromatography (GC) or GC/MS analysis. As shown in FIG. 6(A)-FIG. 6(C) for the headspace GC experiment the syringe (672) used to collect a quantity of gas in the headspace (674) above a liquid sample (689) has a hollow needle (684) connected to the syringe. The needle is inserted into the headspace volume (674) by pushing the syringe down so that the needle passes through a flexible septum (643) which is pierces. The septum acts to maintain separation between the outside atmosphere and the headspace. A heater block (676) is often used to increase the temperature of the sample vial so that volatile molecules from the sample (689) into the headspace. The headspace sample is drawn into the volume of the syringe (672) by pulling on the syringe plunger (670) as shown in FIG. 6B. In FIG. 6A the plunger in depressed before the syringe is pushed through a septum (643) into the headspace region (674) of the sample vial (693). In FIG. 6B the plunger in withdrawn and a portion of the headspace gas drawn up into the syringe (672). The syringe (672) containing the headspace sample is withdrawn from the sample vial by pulling the syringe away from the vial thus removing the needle from the sample vial. In the GC experiment the headspace sample is transferred from the syringe volume into a heated region identified as the injection port (680) as depicted in FIG. 6C by first inserting the needle of the syringe (684) through a flexible septum (645) and then depressing the syringe plunger (670) to expel the gas. Inside the heated injector port a glass liner (678) is used to isolate that the headspace gases from the metal of the heater and this inert liner is designed to minimize retention of chemicals for any length of time. In the gas chromatography instruments the injector volume (678) is maintained at a high temperature in order to efficiently vaporize the compounds from the sorbent coated fiber. Once vaporized the sample exits the injector as the force of flowing gas under high pressure pushes the chemicals through a pressurized fitting (681) into the gas chromatography column (682) which permits separation of two or more of the individual chemicals in the sample from one another. After the individual chemicals spend time in the separation device they exit it and are transferred into the detector for analysis.

In an alternative application the sorbent coated fiber can be inserted into a sample injector loop typically fashioned from a small length of narrow bore capillary tubing in order to complete introduction of a liquid chromatography (LC) or LC/MS system for analysis.

In order to complete the introduction of sorbent coated fiber into either the heated, pressurized GC injector, or the loop of a LC system the SPME fiber is protected from interaction with the injector by positioning it inside a needle (672). The rigid needle is used to puncture the flexible septum (680) which is used to seal this injector hole so that chemicals desorbed from the SPME fiber can only exit the injector by moving into the chromatographic injector volume. Therefore keeping the pressure inside the injector while the needle encasing the SPME fiber is introduced into the injector volume and until the sample is desorbed from that fiber and directed onto the separation column is critical to the prior art. Once the needle has penetrated through the septum the SPME fiber is pushed out of the needle into the open volume of the injector where the heat effects rapid desorption of all chemicals previously bound by the sorbent. The requirement for a syringe needle to be rigid and not bend when being pushed into and through the septum results in the diameter of that metal tube being between approximately 0.2 mm to approximately 0.5 mm. The SPME fiber in prior art therefore does exceed the inside diameter of the syringe. The most popular Solid phase micro extraction (SPME) fibers are commercially available as a polyimide fiber, approximately 300 micron in diameter, with a single type of sorbent materials bound to the surface.

Figure 8:
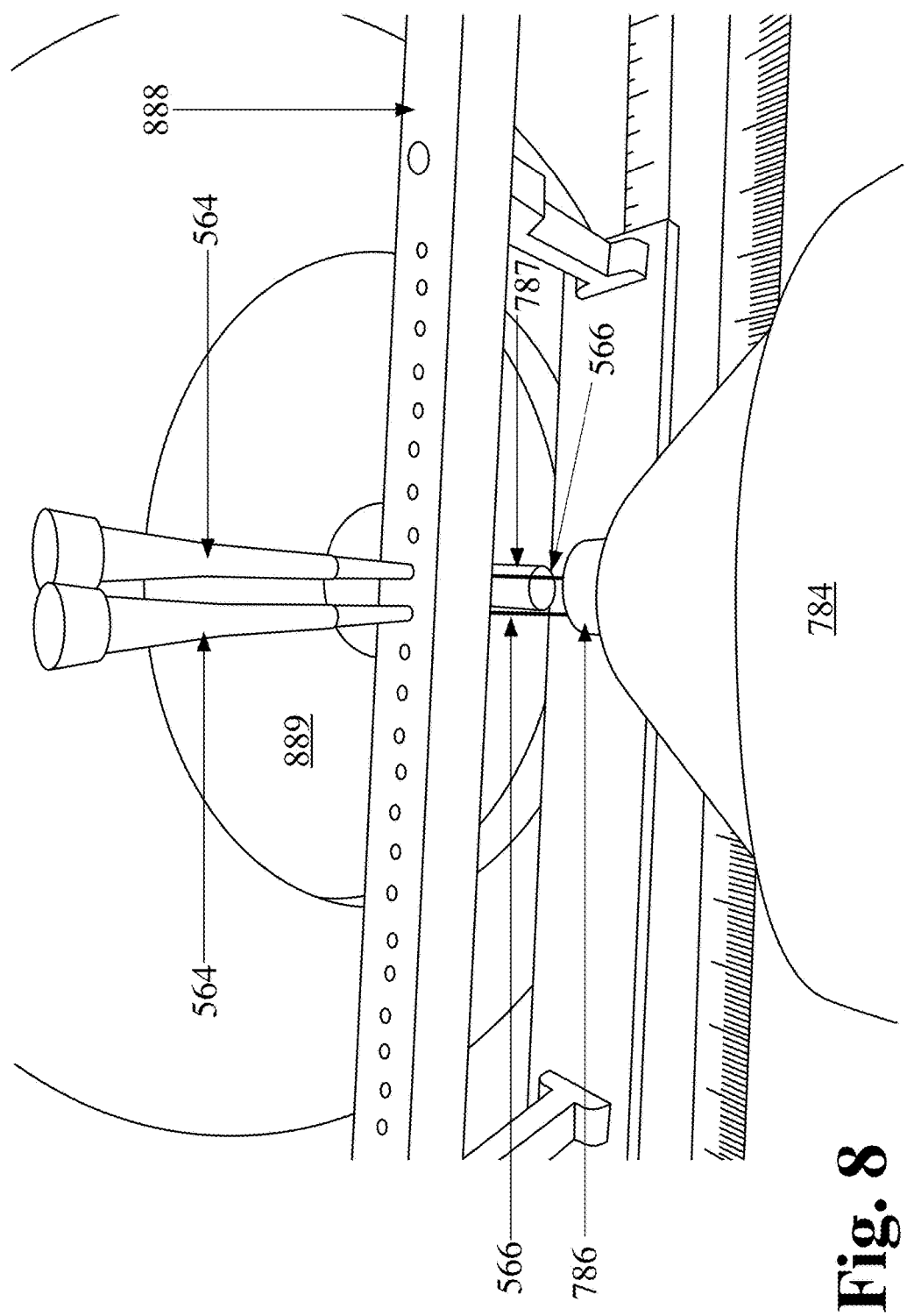
FIG. 8 depicts a schematic of two SPME fibers (566) attached to conventional pipette tip holders (564) inserted into a sample carrier (888) where each SPME fiber is separated by approximately 3 mm so that the fibers can be positioned in the ionization region between the gas exit (786) of the ionizing source (784) and the inlet (787) of the spectrometer (889), according to an embodiment of the invention.

The development of open air ionization systems such as DART and desorption electrospray ionization (DESI) have enabled the direct desorption and detection of chemicals bound to the sorbent fibers. These methods eliminate the sample injector requirement from the experiment. In prior art experiments plasma-based ambient ionization including Atmospheric pressure chemical ionization, direct analysis in real time, and dielectric barrier discharge mediated ionization have been utilized for ionization of compounds directly from different types of sorbent materials used for solid phase extraction in bulk form instead of thin films. In those experiments the liquid containing a sample was drawn into the sorbent material encased in a syringe and allowed to incubate for a limited amount of time. A series of solvent washes and changes of solvent permit removal of salts and non-targeted sample related chemicals from the bulk material present in the sample of analytical interest. In the DART experiment the temperature of the ionizing gas can be varied using at least one of two methods. Firstly, a heater incorporated into the source can be used to heat the carrier gas. Secondly, the sample molecules can be applied to a mesh and the mesh heated. In an embodiment of the present invention the carrier gas is heated for the experiment. In practice varying the desorption gas temperature permits a more complete thermal desorption of the sample by enabling analysis of the same sample at multiple temperatures thus providing for ionization of a wider range of compounds of interest in that sample. In an embodiment of the experiment, DART-based desorption ionization from the SPME device can be used to either completely vaporize the chemicals on the fiber or complete a slower distillation of those same chemicals by first operating at a lower temperature and then changing to a higher temperature. This thermal desorption occurs in close proximity to the atmospheric pressure inlet (API) of an LC/MS or LC/MS/MS. In some experiments the SPME fibers are presented to the ionizing gas by using either a manual introduction system as shown in FIG. 7 or a robotic sample positioner as depicted in FIG. 8. In FIG. 7, the SPME fiber (568) is moved into the desorption ionization region between the heated gas exit (786) of the ionizing source (784) by pushing the holder (783) along a guide. Ions formed by desorption from the fiber enter the inlet tube (787) of the spectrometer for analysis.

The use of the ambient ionization systems decreases the time required for analysis of each SPME fiber thus reducing the time required for sample analysis and in many cases sample preparation requirements. As its utility of the SPME method has grown the types of sorbents available have increased. Unfortunately, the use of one sorbent per fiber per analysis has been the dominant method because of the requirement that the sample be introduced into a narrow injector port. That is the previous rule of use was that one SPME fiber was used per experiment in either GC, LC, GC/MS or LC/MS. Commercial vendors of the SPME fibers developed mixed-mode fibers in order to facilitate collection of a wider range of chemical functional groups on a single fiber. These fibers have two or more different sorbents on their surface. Initial DART-MS experiments using these mixed-mode SPME fibers to collect two different types of chemicals present in samples yielded poor data consistent with the presence of only a single compound. That is, a significant discrimination against some chemicals extracted by the second sorbent was observed. It was hypothesized that the chemicals extracted by the different sorbents were interacting with the ionizing gas and those chemicals with high proton affinities were scavenging the available protons in the ionizing gas resulting in only those high proton affinity molecules being detected in the DART-mass spectrum. This competitive ionization condition has previously been called the "matrix effect" in liquid chromatography/mass spectrometry.

The use of more than one sorbent as a means to collect a wider range of chemical entities for chemical characterization of a sample is desirable because it can result in the collection of a wider variety of chemical entities which, once analyzed, will generate a more comprehensive list of the chemicals present in the original sample. Combining the information from two or more different analyses of the same material results in the development of a chemical signature for that material. In order to examine the optimum positioning required to reduce or eliminate matrix effects between fibers relative to one a series of desorption ionization experiments were completed using four different fiber holders, similar in design to the 3 mm spacing fiber holder (888) shown in FIG. 8. The other holders were produced with spacing between samples of approximately 9 mm, approximately 2 mm and approximately 1 mm. The various fiber holders provided a means to reliably position the fibers ion the ionization region between the gas exit (786) of the ionization source (784) and the inlet (787) of the spectroscopy system (889) were used for a series of experiments some of which are described below.

Experiment 1

Figures 9C, 9D:
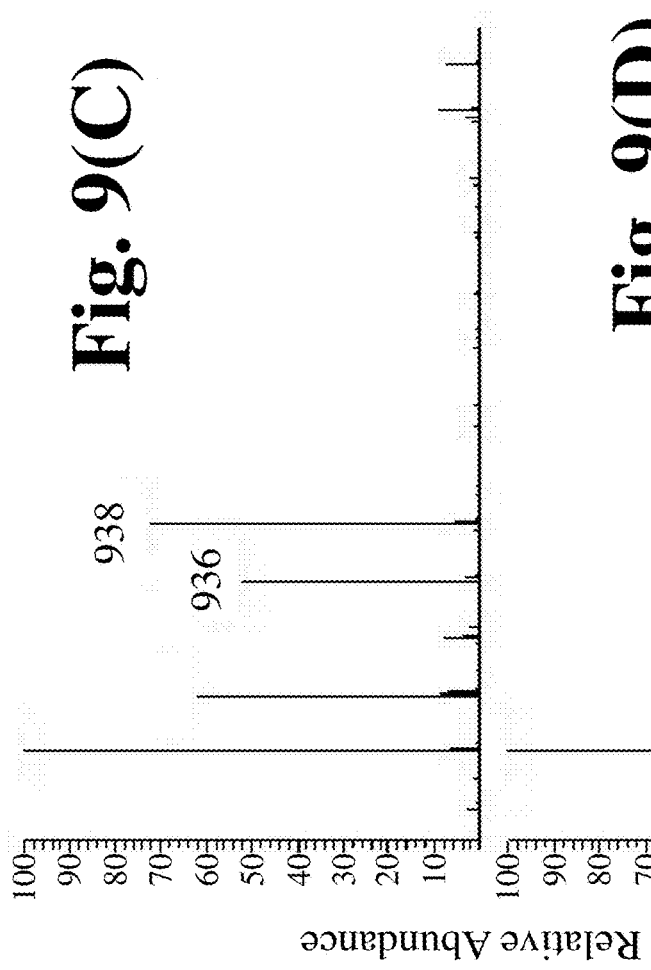
FIG. 9(C) depicts a mass spectrum generated by desorption ionization of an SPME fiber with a different sorbent coating to the SPME fiber measured in FIG. 9(D) and separated by approximately one (1) mm from the different sorbent coating to the SPME fiber measured in FIG. 9(D) in the 'Closeness Test for Matrix Effects', according to an embodiment of the invention.
FIG. 9(D) depicts a mass spectrum generated by desorption ionization of an SPME fiber with a different sorbent coating to the SPME fiber measured in FIG. 9(C) and separated by approximately one (1) mm from the different sorbent coating to the SPME fiber measured in FIG. 9(C) in the 'Closeness Test for Matrix Effects', according to an embodiment of the invention.

A solution containing glucose and the drug benzocaine was extracted using a first multi-sorbent coated SPME fiber and a second single-sorbent coated SPME fiber. The first fiber had both C-18 and a cation exchange sorbents, while the second fiber had a C-18 sorbent. Thus the first SPME fiber can extract a wider range of chemicals with different physical properties than the second SPME fiber. The first and second fiber were sequentially presented into the desorption ionization region passing through it at a constant rate of speed in an embodiment of the invention. Depending on the holder used the fibers were separated by: approximately 9 mm, approximately 3 mm, approximately 2 mm or approximately 1 mm, where approximately in this range means plus or minus ten (10) per cent. The mass spectrum generated by desorption ionization of the two different fibers separated by approximately 9 mm of space are shown in FIG. 9(A) and FIG. 9(B). Unexpectedly, the major ions produced by glucose are detected at m/z 180 (936), and m/z 197 (938) and the major ion for benzocaine is detected at m/z 166 (934). The mass spectra are clearly different although the glucose related ions 936 and 938 are present in both data. In subsequent experiments, as the individual fibers were positioned closer to each other during ionization the relative abundance of the protonated benzocaine detected at m/z 166 decreases until at 1 mm separation it is no longer detectable. Unexpectedly, as the separation decreases the mass spectra become nearly identical as shown in FIG. 9(C) and FIG. 9(D) where benzocaine is not detected and the glucose related ions are very abundant. At the time of carrying out these experiments, it was not known or expected that the spectra from different surfaces separated by 1 mm can be effected by the presence of the other surface in a desorption ionization experiment. In an embodiment of the invention, as the separation between the fibers was decreased below approximately 1 mm the resulting data can no longer be differentiated from one another by using the desorption ionization mass spectrum. As a result, the capability to detect the active drug component in a sample can be compromised if the fibers are analyzed in too close proximity to each other. Mass chromatograms plot the relative abundance of the different ions as a function of fiber separation during desorption ionization, as shown in FIG. 10. The relative abundance of the protonated benzocaine at m/z 166, which is only extracted from the solution by the first fiber, is shown in the top panel FIG. 10 (A). Initially, with the 9 mm spacing between fibers, the protonated benzocaine at m/z 166 ion abundance (see FIG. 10(A) mass chromatogram) is significant as the first fiber, the fiber having which has a mixed mode sorbent composition, enters the ionization region at 0.3 minutes and then disappears at 0.4 minutes until the second fiber, the single sorbent fiber that does not retain the benzocaine, enters the ionization region at 0.5 minutes. The glucose related ion at m/z 180 ion abundance (see FIG. 10(B) mass chromatogram) is detected at a consistent relative abundance regardless of fiber separation during the ionization experiment. Results from the analysis of the second fiber set, separated by only 3 mm, are presented in the second box. The first fiber of that set enters the ionization region at 1.25 minutes and the relative abundance of the protonated benzocaine m/z 166 ion decreases by more than half relative to the 9 mm separation result. The generation of protonated benzocaine continues to decrease by another factor of 2 when the third set of fibers, separated by only 2 mm, enter the ionization region at time 2.0 minutes. Finally, at the fibers separated by only 1 mm enter the ionization region at 2.7 mm the protonated benzocaine is barely detected In an embodiment of the invention SPME fiber placement must be sufficient to reduce or eliminate the simultaneous desorption of analyte from adjacent fibers in order to facilitate independent ionization of all molecules retained by each of the fibers in order to reduce or eliminate matrix effects.

In an alternative embodiment of the invention, multiple fibers with mixed sorbents were analyzed at different positions with a minimum spacing required in order to isolate the fibers from each other. A person of ordinary skill in the art would understand that the spacing can be determined by factors selected from the group consisting of the ionization affinity of the components in the sample, the vapor pressure of the components in the sample the heat of enthalpy of the components in the sample, the entropy of the components in the sample and other factors affecting the gas phase volatility of the components in the sample. Analysis with a spacing of between approximately 1 mm and approximately 10 mm can present obvious starting points for determining the required spacing. In various embodiments of the invention, the spacing between fibers can be reduced to as little as approximately 0.1 mm as by using different desorption ionization sources having smaller ionization region requirements. Those sources include, but are not limited to, atmospheric pressure chemical ionization, laser desorption, and desorption electrospray ionization which have capability for desorption ionization from areas of as little as approximately 100 micron. In another embodiment of the invention, multiple fibers with different sorbents were simultaneously analyzed at different positions by using multiple ionizers. In another alternative embodiment of the invention, multiple fibers with different sorbent type SPME fibers contacted with mixed sorbents were simultaneously analyzed at different positions. Independent desorption can result in ionization of the different molecules from the sample.

Experiment 2

In LC/MS analysis the matrix effect is often eliminated by utilizing chromatography to separate the molecules from each other prior to their arrival in the ionizing region of the instrument. The chromatographic material permits separation of matrix components from the compounds of interest as those components bind to the chromatographic material for a longer time period than the matrix components thus physically resolving one component from analysis at the same time as another component. In the desorption ionization experiment, rather than using a physical separation to remove the matrix compounds the thermal properties of the different compounds in a sample including; matrix and compound of interest, are leveraged to permit detection of a more representative chemical signature for the sample. Analyzing the same sample by exposing it to the ionization gas at a series of increasing temperature values serves to reduce the matrix effect by removing the low temperature volatile matrix molecules prior to desorption of the larger, more analytically useful molecules, namely those that desorb at the higher temperatures. This experiment is referred to as thermal profiling of the sample. The thermal profile can be generated with samples desorbed from either inert or sorbent coated surfaces.

In practice exposure of the SPME fibers to the ionizing gas may involve movement of the fiber into and out of the gas region several times. In this case a region of the fiber that has already been exposed to a low temperature ionizing gas will subsequently be exposed to the higher temperature gas along with the a previously unexposed section of the fiber in very close proximity.

Figure 13A:
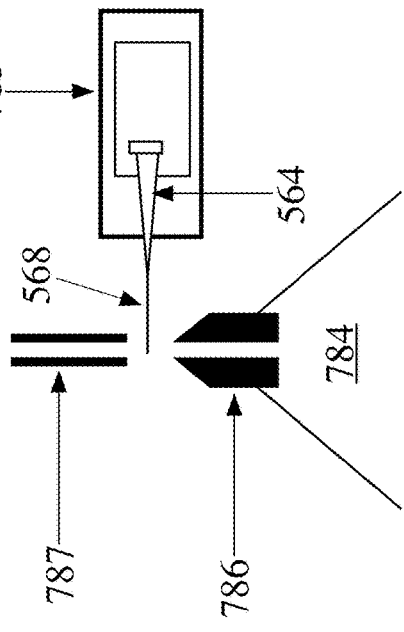
FIG. 13(A) shows multi-temperature SPME DART robotics MS analysis of a fiber at an initial position where fiber is not exposed to ionizing gas, according to an embodiment of the invention.
Figure 13B:
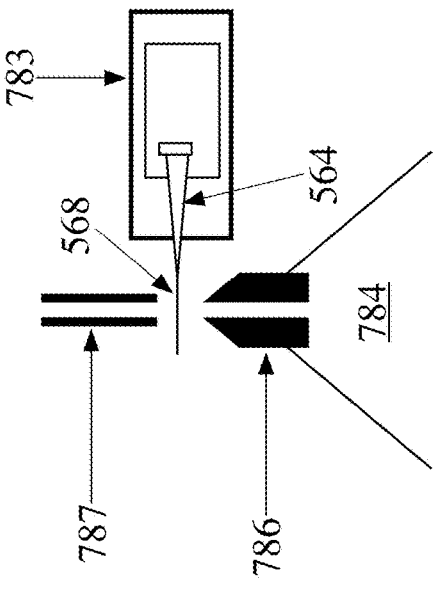
FIG. 13(B) shows multi-temperature SPME DART robotics MS analysis of a fiber at first exposure where first short segment of fiber is exposed to ionizing gas, according to an embodiment of the invention.
Figure 13C:
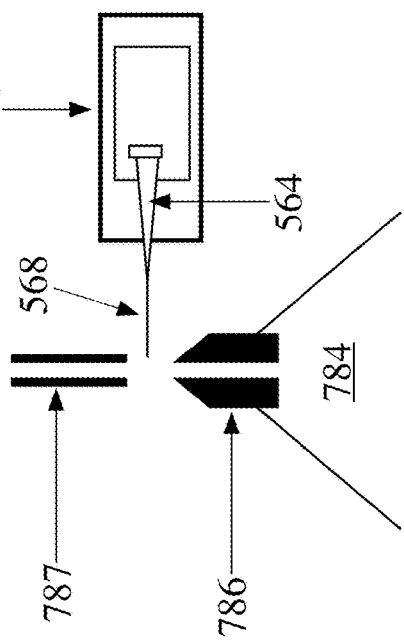
FIG. 13(C) show multi-temperature SPME DART robotics MS analysis of a fiber at second exposure where second short section adjacent to first short section of fiber is exposed to ionizing gas, according to an embodiment of the invention.
Figure 13D:
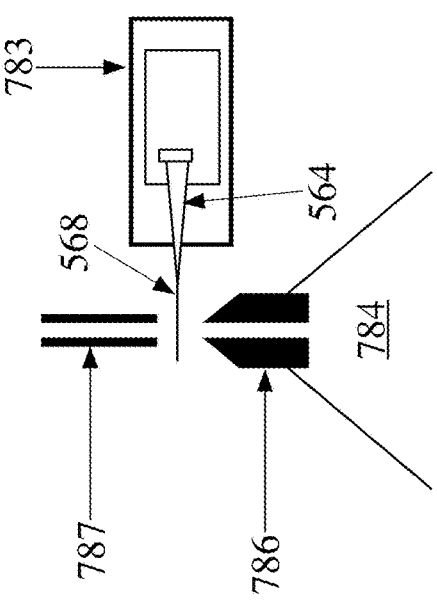
FIG. 13(D) show multi-temperature SPME DART robotics MS analysis of a fiber at third exposure where third short section adjacent to second short section of fiber is exposed to ionizing gas, according to an embodiment of the invention.

In an embodiment of the invention, the same fiber can be analyzed at multiple temperatures in order to (i) potentially reduce the matrix effects that might be observed and (ii) enable a more rapid and cost effective analysis that requires only one fiber to desorb multiple types of compounds in a single experiment. Results from the analysis of a mixture of chemicals including: quinine, acetazolamide and rhodamine B on a single SPME fiber after exposure at five different temperatures are shown in FIG. 11, where the total ion chromatogram FIG. 11(A), and ion chromatograms for three target chemicals protonated rhodamine B at m/z 443 FIG. 11(B), protonated quinine at m/z 325 FIG. 11(C) and protonated acetazolamide at m/z 223 FIG. 11(D), known to have different optimal thermal desorption temperatures, are displayed as a function of the desorption ionization gas temperature. A PDMS-divinyl-benzene coated SPME fiber was used for this experiment; however any fiber can be used provided it collected the material of interest. DART gas temperature was approximately 100° C. when a small section of the distal end of the SPME probe was inserted into the desorption ionization region from time zero to one minute; the probe was then withdrawn from the region. The DART gas temperature was raised to approximately 150° C., approximately 200° C., approximately 250° C., and approximately 300° C. with the probe being reinserted further into the ionizing region at each increasing temperature so that a previously unexposed section of the sorbent was subject to interrogation using the hotter desorption ionization gas. As in the first experiment sequence described above, the probe was withdrawn from the region while the gas temperature was raised to each new temperature. Mass spectra generated during exposure of the PDMS-divinyl benzene fiber SPME probe to different desorption temperatures are shown in FIG. 12 at approximately 100° C. FIG. 12(A), approximately 250° C. FIG. 12(B) and approximately 300° C. FIG. 12(C). In FIG. 12(A) the component with the maximum relative abundance is Acetazolamide (peak 1201). In FIG. 12(B) both quinine (peak 1204) and rhodamine B (peak 1202) are detected while rhodamine B (peak 1202) dominates the mass spectrum acquired when the desorption gas temperature is 300° C. FIG. 12(C) see peak 1202. The mass spectra demonstrate that the utility of the single fiber experiment as a means to thermally desorb different materials for analysis at different times. A schematic of the desorption ionization region into which the single elongated SPME fiber has been inserted to four different lengths in order to carry out the multiple temperature, single fiber experiment, is shown in FIG. 13. In FIG. 13 a multi-temperature SPME DART robotics MS analysis of a fiber at an initial position where fiber is not exposed to ionizing gas is shown in FIG. 13(A), a first exposure where first short segment of fiber is exposed to ionizing gas is shown in FIG. 13(B), a second exposure where second short section adjacent to first short section of fiber is exposed to ionizing gas is shown in FIG. 13(C), and a third exposure where third short section adjacent to second short section of fiber is exposed to ionizing gas is shown in FIG. 13(D).

Experiment 3

In the prior art SPME-MS experiment a new fiber would be required for each sample presented for analysis since desorption of all the chemical entities on the entire fiber is completed at a single temperature in an injector as shown in FIG. 6(C). By design, the injector of a GC or LC system can accommodate only one fiber thus limiting direct interrogation of the sample to one analysis. In an embodiment of the present SPME-DART analysis invention, the thermal profile experiment can be completed using multiple fibers with a different fiber being analyzed at each desorption ionization temperature setting. SPME fibers are immersed in a solution so that the entire length of the sorbent coated surface was immersed in the volume of solution containing the sample, such that retention of sample along the length of the SPME fiber is uniform. Following an appropriate extraction period the individual fiber is removed from the sampling container. The series of SPME fibers (566) were mounted into the automated sampler comprised of a linear rail (1491), and SPME mounting module (1490) positioned such that the SPME fiber sorbent surface passes between the ionizing source exit (786) and spectrometer entrance (787) are presented for analysis at measured intervals so that, most critically, no two fibers can be positioned in the desorption source (785) ionization region at the same time. A model of the system is shown in FIGS. 14(A) and 14(B). In a typical SPME-based sample by using desorption ionization for the analysis a single fiber is sufficient for a single analysis, in an embodiment of the invention the experiment is not completed until multiple fibers have been analyzed and the combined information is integrated to describe all of the chemicals detected in the sample In various embodiments of the invention, a desorption ionization thermal profile measurement of a sample is completed using desorption gas heated to a plurality of different temperatures with mass spectra collected in positive ion and negative ion mode at each temperature. In an embodiment of the invention, a thermal profile measurement of a sample is analyzed using desorption gas heated to three different temperatures. The Thermal Profile is formed by the collection of three positive ion and three negative ion mass spectra. Alternately, as not all spectrometers have negative ion detection capability a Thermal Profile may contain only positive ion mass spectra. Similarly, for some classes of compounds, only negative ions might be produced leading to a Thermal Profile that contains only negative ion mass spectra. The compiled data collected in all of these possible configurations form the thermal profile of the material. Predictably compounds that vaporize at lower temperature will appear in the low temperature mass spectra while the less volatile materials will be detected at higher temperatures. Given a system with good temperature control all of the SPME fibers (566) will be analyzed in a short time interval with the same temperature gas for each sample probe presented into the desorption ionization region FIG. 14.

Figures 19A, 19B, 19C:
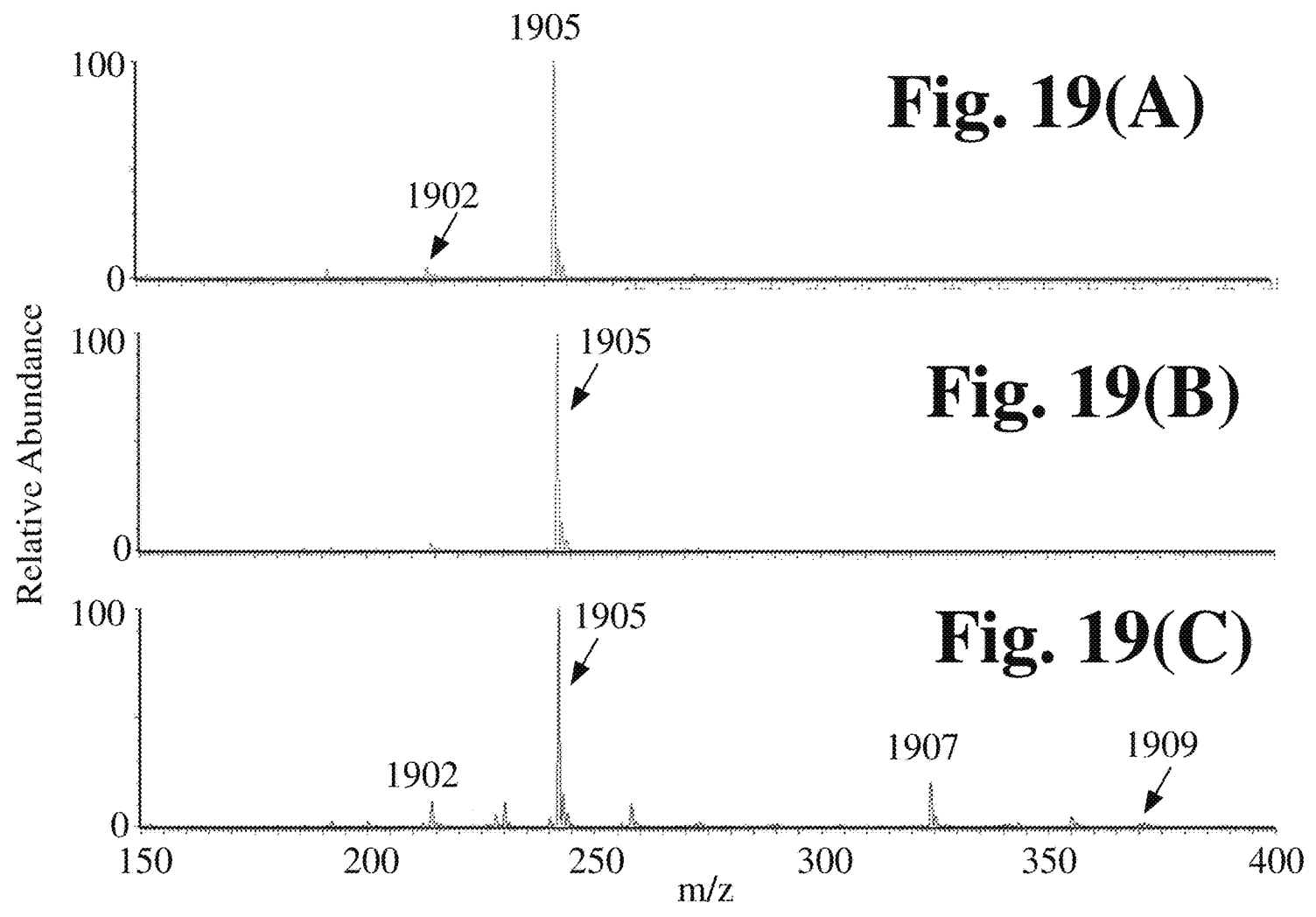

In an embodiment of the invention three SPME fibers (FIG. 14(A) (566) were used to extract mixtures of pesticides and narcotics from a sample of commercial synthetic urine which is known to contain several of the major chemicals in urine and no narcotics or pesticides. In the experiment the three fibers loaded with sample were pushed through the ionization region where the desorption ionization gas was 100° C. for the first 150 scans, then 200° C. from scan 295 to 425 and finally 300° C. from scans 630 to 750 where desorption of the targeted narcotics occurs. The same region of the fiber was exposed to the ionizing gas at each temperature setting. The sample laden SPME fiber were positioned side-by-side in the SPME module (888) mounted on the motorized linear rail (1491) and the motorized rail was turned on and pushed the module resulting in the three SPME fibers entering the desorption ionization region between the source exit (786) and the and the spectrometer entrance (787) region. A desorption gas temperature of 100° C. was used for the initial experiment. Mass spectrum acquired from the first SPME fiber is shown in FIG. 19(A). Species were observed at 1902 (m/z 214) and 1905 (m/z 242) representing the volatile pesticide molecules were detected. The two pesticides, Cyanazine, and Desmetryn were detected with good sensitivity at both 100° C., 200° C. and 300° C. The increase in desorption gas temperature to 300° C. results in the ionization and detection of the drugs which were also extracted from the sample by the SPME fiber. The mass chromatogram for the protonated pesticide Cyanazine m/z 242 is shown in the trace of FIG. 20(C)(i). The pesticides were detected on all three SPME fibers in that first sample set. The narcotics, known to be present, were not detected so the desorption gas temperature was increased to 200° C. After the DART gas temperature stabilized the SPME fibers were once again pushed through the desorption ionization region. In this case only the pesticides were detected once again as shown in the mass spectrum in FIG. 19(B). The mass chromatogram for the protonated pesticide Cyanazine m/z 242 desorbed using 200° C. gas is shown in the trace of FIG. 20(C)(ii). Still seeking to detect the narcotics the DART gas temperature was increased to 300°. Once the DART gas temperature stabilized at the third, higher temperature, the SPME fibers were again pushed through the desorption ionization region for analysis. In an embodiment of the invention, the 300° C. gas was sufficient to permit desorption ionization of the low vapor pressure drug compounds that were not detected at lower temperatures as well as some pesticide residues that remained on the fiber due to incomplete desorption at the lower gas temperatures. The mass spectrum in FIG. 19(C) shows 1902 (m/z 214), 1905 (m/z 242), 1907 (m/z 324), 1909 (m/z 373). These species represent the protonated molecule for heroin (1909), LSD (1907), Cyanazine (1905), and Desmetryn (1902). Operation at higher temperatures can be used to enhance the detection of those narcotics, despite the fact that their relative abundance when compared to the pesticide Cyanazine is low, the mass chromatograms for the protonated molecules of heroin and LSD are strong and steady as shown in FIG. 20(A) and FIG. 20(B). The mass chromatogram for the protonated pesticide Cyanazine m/z 242 desorbed using 300° C. gas is shown in the trace of FIG. 20(C)(iii).The use of sequential desorption at different gas temperatures thus has two benefits (1) it permits detection of different molecules at different temperatures and (2) it improves the sensitivity for detecting chemicals in a mixture by reducing the abundance of molecules desorbed at any one time based on volatility.

Figure 21:
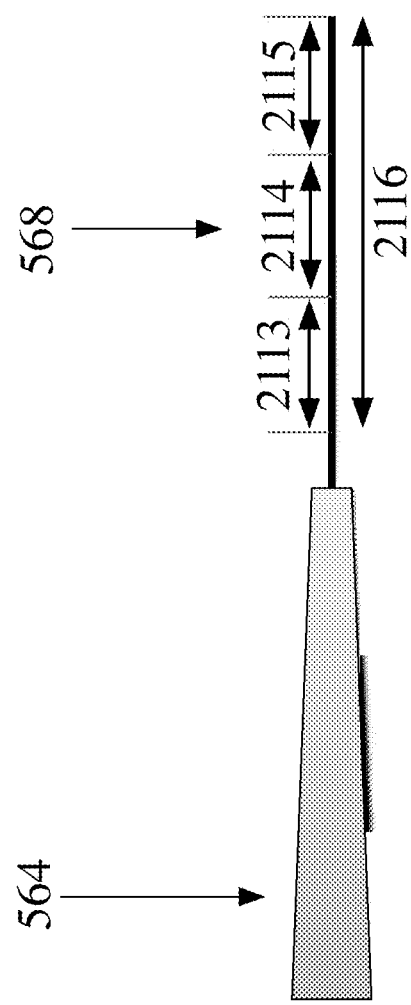
FIG. 21 shows a diagram of the SPME fiber assembly of FIG. 5 with three areas on the fiber tip, according to an embodiment of the invention.

FIG. 21 shows a SPME tip, where according to various embodiments of the invention, the total length 2116 of the tip 568 can be divided up into a plurality of regions for analysis. In FIG. 21 the tip 568 is divided up into three lengths 2113, 2114 and 2115. In an embodiment of the invention, the three lengths 2113, 2114 and 2115 are equal. In an embodiment of the invention, the tip is 9 mm in length and 2113, 2114 and 2115 are each 3 mm in length. In an alternative embodiment of the invention, the three lengths 2113, 2114 and 2115 are not equal.

In an embodiment of the experiment a series of different sorbent coated fibers are used to isolate targeted molecules from a sample. Each of the different sorbent fibers is analyzed independently at the same temperature or a thermal profile experiment can be completed for each fiber.

In an embodiment of the invention, a screen fabricated from sorbent coated wire replaces the sorbent fiber for sampling FIG. 15(A). The sorbent coated screen has the advantage sampling from a greater surface area in the same time period as a single fiber. In an embodiment of the invention, a large surface area screen can have different regions coated with different sorbents. The multi-sorbent screen can be exposed to the same sample in the same container in order to complete the SPME experiment. Desorption ionization of different sections of the wire mesh can be completed using either the same or different temperatures. The different sections of the mesh can be separated by either application of sorbent to different sections or by removing sections of the sorbent coated wire.

In an embodiment of the experiment a piece of sorbent coated wire mesh are positioned in a sample carrier FIG. 15(B). The carrier body (1592) permits positioning of the sample laden wire mesh in the desorption ionization region between the gas exit of the ionizing source and the inlet of the spectrometer. Multiple wire mesh from either different samples or the same sample can be analyzed by placing one piece of mesh into each slot (1594) and (1595) and pushing those wire mesh through the desorption ionization region sequentially if desired.

In an embodiment of the invention a thermal desorption profile can be generated by using a collection of wire mesh that have been exposed to the same sample, placing one wire mesh in each of the even numbered slots (1594) of the carrier (1592). Analysis of the first sample is completed at the starting temperature after which the carrier is pushed along its axis until the desorption ionization region is aligned with the odd number slot (1595) which is empty. While positioned with the empty slot in the desorption ionization region the gas temperature can be raised to the higher temperature necessary for the analysis of the second sample without consuming that sample. Once the temperature reaches the second desired temperature the second wire mesh laden with sample is moved by the carrier to a position where it is in the desorption ionization region. The process is repeated as desired to fully characterize the sample.

In an embodiment of the invention screens coated with different sorbents that have been exposed to the same sample can be mounted in the carrier and analyzed in order to generate more comprehensive results from the analysis of that single sample.

In an embodiment of the invention the width and height of the wire mesh can be less than the total volume of the open space of each position (1595) in the carrier (1592).

Figure 16:
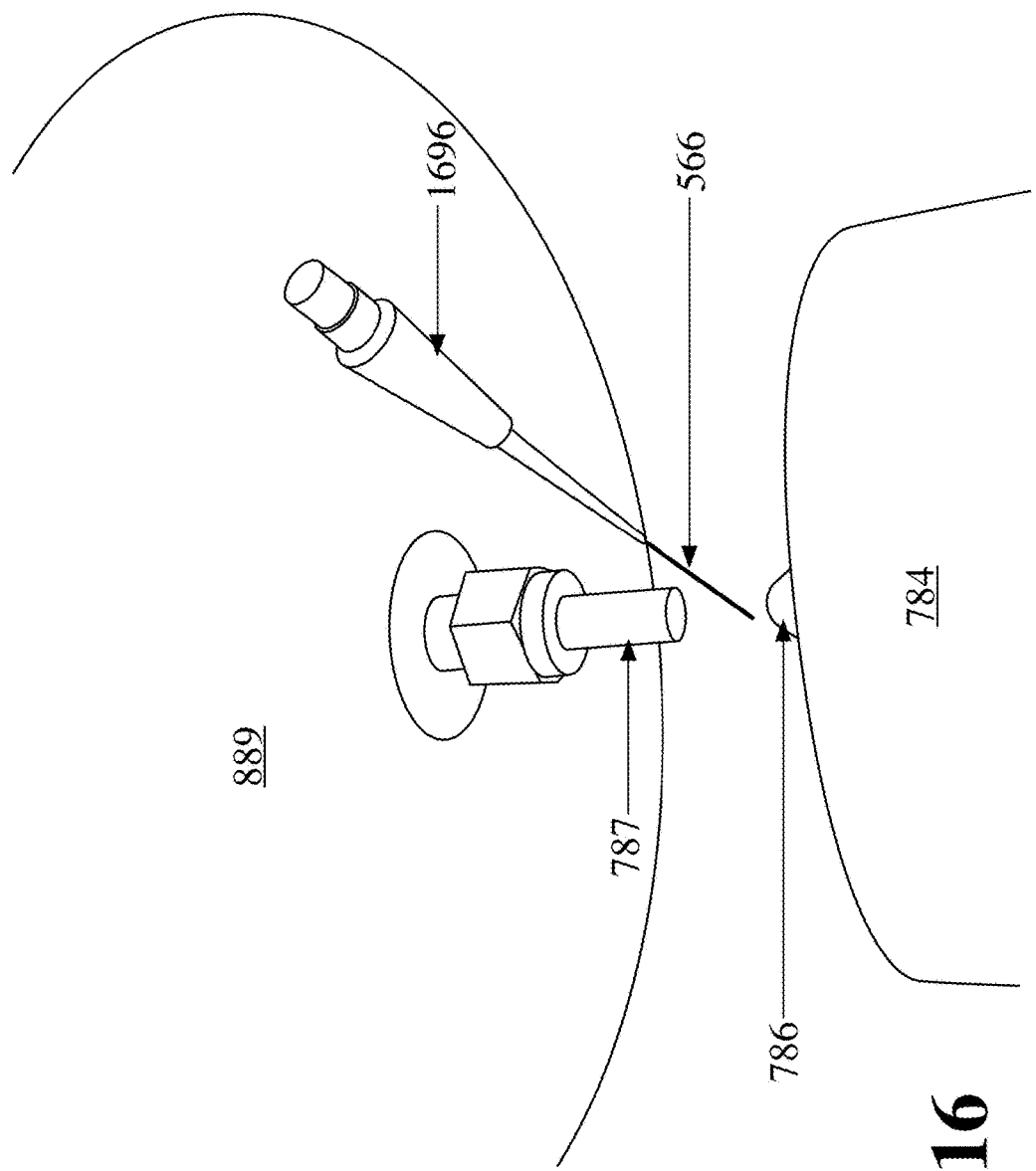
FIG. 16 depicts a schematic of a SPME fiber (566) mounted in a sampler needle assembly (1696) which was held so that the fiber was inserted into the ionization region between the gas exit (786) of the ionizing source (784) and inlet (787) of the spectrometer (889), according to an embodiment of the invention.
Figure 17:
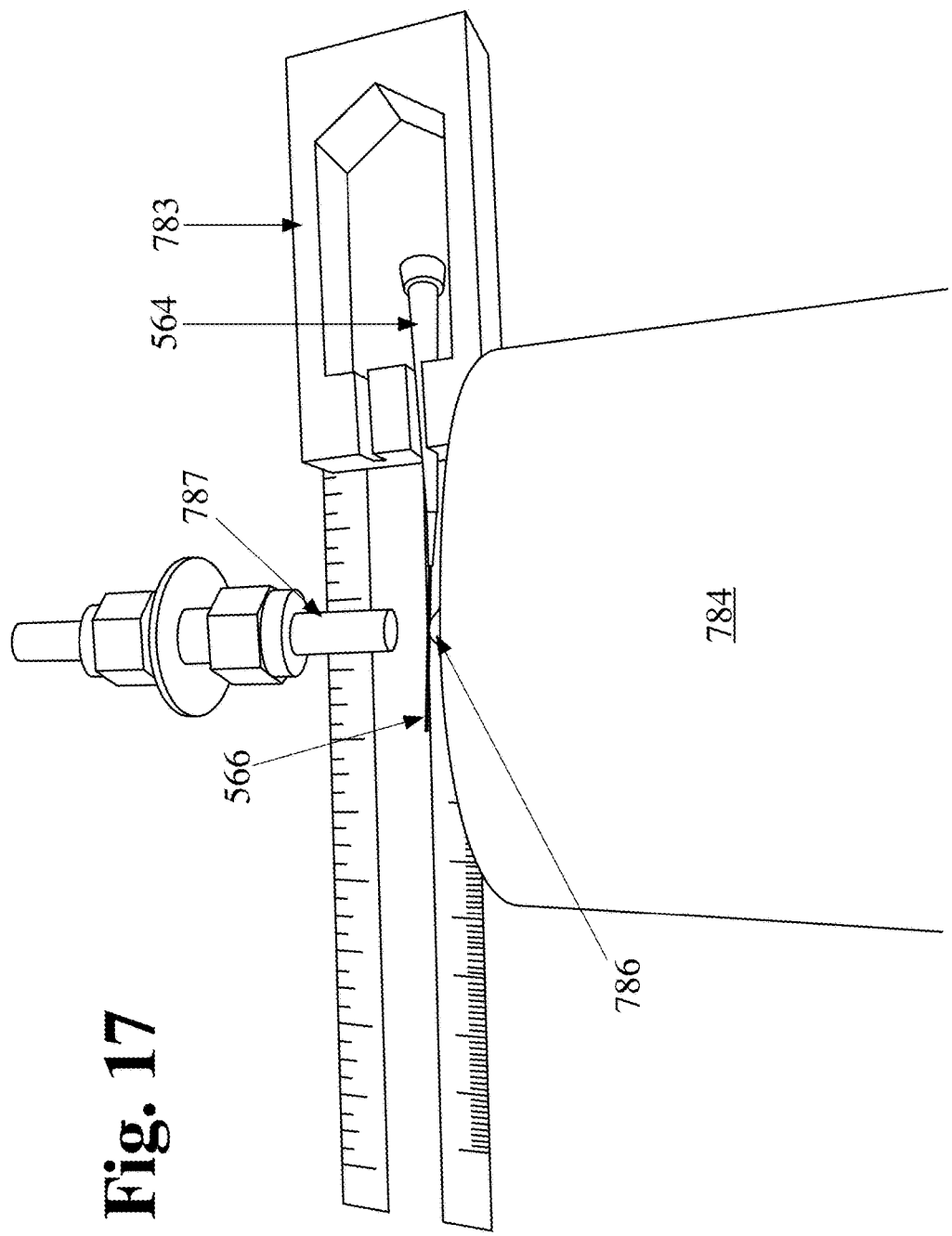
FIG. 17 depicts a schematic of a fiber held by a digitally operated module (783) designed to hold either the short SPME fiber (566) or the elongated SPME fiber (568) in-line with the ionization region between the gas exit (786) of the ionizing source (784) and inlet (787) of the spectrometer, according to an embodiment of the invention.

In an embodiment of the experiment the sorbent fiber is a long fiber (FIG. 5(B)). The long fiber is utilized in order to enable multiple analyses from the same fiber with different temperature DART gas. The position of the fiber can be adjusted manually FIG. 16 or by robotic means FIG. 17 between analyses so that different regions of the fiber can be exposed to the gas. The device shown in FIG. 5(B) has a fiber of sufficient length so that the sorbent region in the desorption ionization region is unique for each temperature.

In an embodiment of the invention the sorbent coated mesh is fashioned into a cylinder that wraps around a solid material such as a wire or fiber. The mesh can be present as an extension of the syringe plunger for example.

Experiment 4

Thin layer chromatography (TLC), is commonly used to permit a visual separation of chemicals contained in a sample from each other by using a thin film of sorbent. Generally in TLC, the sorbent is an inorganic material bound to the surface of a glass plate, metal plate or plastic surface by physical and/or chemical forces. The TLC experiment is undertaken in a series of steps: (i) spotting of the sample to the sorbent coated surface a short distance from its proximal end, (ii) immersion of the proximal end into a tall container having a volume of the solvent that is less than sufficient to reach the spot of the sample, and (iii) allowing the solvent to be absorbed by the sorbent and thereby move the sample up the surface based on the chemical interaction of different components in the sample with the sorbent. Different components therefore are separated from each other based on their structure, solubility, binding characteristics as well as chemical composition. In another embodiment of the present invention, the function of the SPME fiber or mesh is therefore similar to the function of the thin layer inorganic materials bonded to glass plates or plastic surfaces of thin layer chromatography (TLC) devices.

When conducting the multi-temperature SPME desorption ionization experiments it was noted that at the same desorption gas temperature the same chemicals took longer to desorb from by the SPME fiber than from the typical glass tube. Desorption ionization off of a glass surface can often results in a brief desorption event, that means desorption of the sample is complete in a short interval of time (e.g., less than approximately 10 seconds) provided the material being analyzed has a sufficiently high vapor pressure and the desorption gas has a sufficient heat to complete vaporization ranging from room temperature to moderate temperature (e.g., approximately 350° C.±25° C.). In this temperature range approximately means plus or minus ten (10) per cent. In the case of the SPME fiber the sample ionization period was observed to be longer than for the same compounds desorbed from glass surfaces. In some cases it was difficult to desorb chemicals completely even at elevated temperatures (e.g., approximately 350° C.±35° C.). In this temperature range approximately means plus or minus ten (10) per cent. To investigate the efficiency of different solvents for removal of chemicals a dye mixture was utilized as the sample, the proximal end of the SPME fiber was dipped into a solvent for short periods of time and analyzed by visual means as well as with DART-MS to detect the rate of removal of the chemical.

After only short exposure times the interval require for removal of dye with strong solvents was observed to be uniform. However, given a longer period of time the removal of dye was observed to be less successful. As those sorbent coated regions had not been immersed in the solvent it seemed that the analyte had migrated up the sorbent coating into the untreated region. When continuing the desorption ionization analysis along the length of the fiber it was determined that some chemicals had been pushed further along the fiber than others essentially presenting the fiber as being capable of completing a TLC based separation experiment.

Experiment 5

Figure 18B:
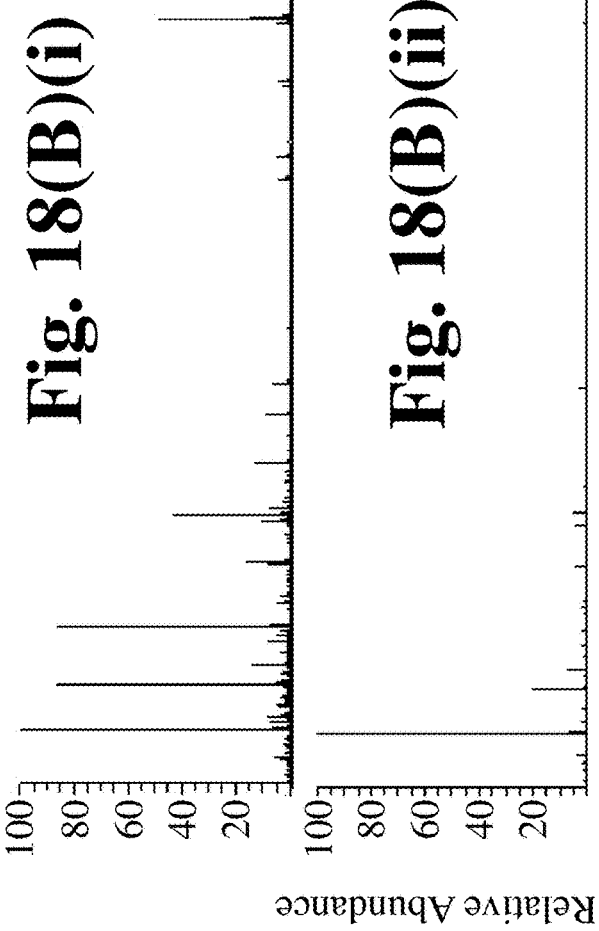
FIG. 18(B)(i) shows the mass spectrum from the analysis of the elongated PDMS-divinyl benzene SPME probe after TLC separation of three components in TLC test mixture, where the spectrum shown was acquired at desorption times of approximately 1.75 minutes and direct desorption ionization from the fiber surface was complete by using helium gas ionized and heated to approximately 250° C., according to an embodiment of the invention.

In an embodiment of the invention, an aliquot of sample was deposited on a small section of the surface of a SPME fiber (see FIG. 5(B)) and allowed to dry. The sample position was at a distance of approximately 2-3 mm from the proximal end of the SPME fiber. The proximal end of the fiber with the sample laden portion was then inserted into a vessel containing a volume of solvent or solvents required for the chromatographic separation. The depth of the solvent was less than approximately sixty (60) per cent of the distance between the proximal end of the fiber and the sample laden position on its surface. The portion of the fiber containing the sample was not immersed in the solvent. As in the conventional TLC experiment the vessel or chamber containing the solvent and the sample laden fiber with its proximal end immersed in the solvent is closed to permit the solvent vapor to rise in the chamber. The interaction of solvent vapor, sample molecule and sorbent chemicals results in the transit of molecules from the proximal to the distal end of the SPME fiber by capillary action. As the solvent front reaches a point near to the distal end of the SPME fiber it is removed from the vessel to stop the separation. Direct analysis of the fiber with DART-MS was undertaken either manually by hand (FIG. 16) or by using fiber holder (FIG. 17) to push the SPME fiber through the desorption ionization region at a steady rate. The results of analysis of a SPME Fiber after TLC separation of three components in a standard TLC test mixture are shown in FIG. 18(A). Direct desorption ionization from the fiber surface as a function of position was completed using helium gas ionized and heated to approximately 250° C. The fiber was pushed through the ionization region at rate of speed of approximately 0.2 mm/second, according to an embodiment of the invention; the large arrow at the top of the figure identifies the point at which the sorbent coated fiber enters the ionization region, the arrow at approximately 1.75 minutes indicates the point of application of the sample where some of those molecules in the sample are not soluble in the solvent and thus do not move, the arrow at approximately 1.95 minutes shows the movement of molecules that are soluble and thus move with the solvent up the fiber and the arrow at approximately 2.5 minutes shows the movement of a molecules that migrates with the solvent but are not well resolved from each other as they may be different isomers which may or may not have different metal atoms in their structure. Mass chromatograms show the relative abundance of ions for three different chemicals m/z 123 see FIG. 18(A)(i), m/z 445 see FIG. 18(A)(ii), and m/z 143 see FIG. 18(A)(iii). Ionization was completed by using desorption ionization with helium gas at 250° C. Fiber speed of presentations was 0.2 mm/second. The mass spectra for each of the major ions are shown in FIG. 18(B) where the mass spectra shown in FIG. 18(B)(i) was acquired for materials which did not move from the starting point at 1.75 minutes, where the mass spectra shown FIG. 18B(ii) is for the material present on the fiber having migrated 1.2 mm up the fiber and where the mass spectra shown FIG. 18B(iii) is for the material present on the fiber having migrated 12 mm up the fiber.

In an embodiment of the invention the SPME fiber can be coated with a variety of sorbents including but not limited to C-18, PDMS/divinyl-benzene, PDMS, C-8, C-4 and other materials commonly used for SPME analysis. In an embodiment of the invention an untreated silica coated fiber can be utilized. In an embodiment of the invention the fiber can be coated with carbon, functionalized carbon, tenax or inorganic materials. In an embodiment of the invention PDMS coated fibers can be used.

In an embodiment of the invention the proximal end of the SPME fiber is immersed in an aliquot of sample in order to extract the chemicals present in that sample as in the conventional SPME operation. The SPME fiber is removed from the sample containing solution. The sample laden SPME fiber is then inserted into a vessel containing a small volume of an appropriate solvent or solvents in order to remove a portion of the sample from its proximal end in order to leave a short length of sample of the fiber for separation by using the SPME-fiber for the TLC analysis. The volume of solvent in the vessel being no deeper than the short distance from the proximal end of the fiber but less than enough to remove the entire sample. Some portion of the fiber containing the sample must not be immersed in the solvent as it might remove the sample. As in the conventional TLC experiment the sample laden SPME fiber is placed in a second vessel to permit the solvent to transit from the proximal to the distal end of the SPME fiber. Separations of the components of the sample are made by interaction of those chemicals with solvents and/or the sorbent on the SPME fiber. As the solvent front reaches a point near to the distal end of the SPME fiber the fiber is removed from the vessel to stop the separation. Direct analysis of the fiber can be undertaken with DART-MS. In an embodiment of the invention the SPME fiber can be coated with a variety of sorbents including but not limited to C-18, PDMS/divinyl-benzene, PDMS, C-8, C-4 and other materials commonly used for SPME analysis. In an embodiment of the invention an untreated silica coated fiber can be utilized. In an embodiment of the invention the fiber can be coated with carbon, functionalized carbon, tenax or inorganic materials. In an embodiment of the invention, the fiber can be PDMS coated.

In an embodiment of the invention a collection of SPME fibers can be affixed to one another in order to increase the surface area available for the experiment. The fibers can be joined at the proximal or distal end or at some position along the fiber in order to create a bundle of fibers.

In an embodiment of the invention, the sample laden SPME fiber can be inserted into a vessel or tube with the proximal end connected to a volume of solvent or solvents that are being continuously evaporated by use of a heating source. The solvent vapor immerses the volume of the SPME fiber flowing in the direction from its proximal to distal end. In an embodiment of the invention one or more SPME fiber can be positioned in the tube or vessel to permit simultaneous TLC. As in the conventional TLC analysis separation of the constituents of the sample are made by interaction of those chemicals with solvent or solvents and the sorbent on the SPME fiber. As the solvent front reaches a point near to the distal end of the SPME fiber the fiber is removed from the vessel to stop the separation.

Experiment 7

In an embodiment of the present invention, chemicals collected by the sorbent can be bound by reversible interactions and can be released when the surface is wetted with solvents in which those chemicals are soluble. For example, interactions between a polar solvent and molecules can be disrupted using acetonitrile. Further, the solvent simultaneously desorbs most of the chemicals from the surface. In an embodiment of the invention, a stream of ionized solvent is directed at the sample laden SPME fiber to permit desorption ionization of chemicals bound to the sorbent fiber for detection. In order to permit desorption of different chemicals from the same fiber the composition of the solvent being emitted from the desorption ionization source is changed over the course of movement of the fiber through the desorption ionization region.

A method of ionizing a sample comprising the steps of receiving a plurality of sorbent coated fibers, each of a length and a diameter to permit multiple exposure of the plurality of sorbent coated fibers, contacting at least one of the plurality of sorbent coated fibers with a sample, separating the plurality of sorbent coated fibers by a distance and directing a plurality of different temperatures of a carrier gas from one or more desorption ionization sources at a target area on the plurality of sorbent coated fiber to ionize molecules present on the target area.

A method of ionizing a sample comprising the steps of receiving a plurality of sorbent coated fibers, each of a length and a diameter to permit multiple exposure of the plurality of sorbent coated fibers, contacting at least one of the plurality of sorbent coated fibers with a sample, separating the plurality of sorbent coated fibers by a distance and directing a plurality of different temperatures of a carrier gas from one or more desorption ionization sources at a target area on the plurality of sorbent coated fiber to ionize molecules present on the target area, further comprising the steps of analyzing molecules with a mass spectrometer in one or both positive and negative ionization modes.

A kit for analyzing a plurality of sorbent coated fibers comprising a plurality of sorbent coated fibers with an average length and an average diameter to permit multiple exposure of the plurality of sorbent coated fibers to a plurality of different temperature gasses from a desorption ionization source, a holder for positioning the plurality of sorbent coated fibers such that the plurality of sorbent coated fibers are separated at least by a distance, where the holder or other means enables contact between the plurality of sorbent coated fibers and one or more samples and a means to adjust a position of one or both the holder and the plurality of sorbent coated fibers such that a plurality of different temperatures of a carrier gas from a desorption ionization source are directed at one or more target areas on the plurality of sorbent coated fibers.

A kit for analyzing a plurality of sorbent coated fibers comprising a plurality of sorbent coated fibers with an average length and an average diameter to permit multiple exposure of the plurality of sorbent coated fibers to a plurality of different temperature gasses from a desorption ionization source, a holder for positioning the plurality of sorbent coated fibers such that the plurality of sorbent coated fibers are separated at least by a distance, where the holder or other means enables contact between the plurality of sorbent coated fibers and one or more samples and a means to adjust a position of one or both the holder and the plurality of sorbent coated fibers such that a plurality of different temperatures of a carrier gas from a desorption ionization source are directed at one or more target areas on the plurality of sorbent coated fibers, where the distance is between a lower limit of approximately 1 mm and an upper limit of approximately 10 mm.

A kit for analyzing a plurality of sorbent coated fibers comprising a plurality of sorbent coated fibers with an average length and an average diameter to permit multiple exposure of the plurality of sorbent coated fibers to a plurality of different temperature gasses from a desorption ionization source, a holder for positioning the plurality of sorbent coated fibers such that the plurality of sorbent coated fibers are separated at least by a distance, where the holder or other means enables contact between the plurality of sorbent coated fibers and one or more samples and a means to adjust a position of one or both the holder and the plurality of sorbent coated fibers such that a plurality of different temperatures of a carrier gas from a desorption ionization source are directed at one or more target areas on the plurality of sorbent coated fibers, where the distance is between a lower limit of approximately 1 mm and an upper limit of approximately 10 mm, where the average length is between a lower limit of approximately 4 mm and an upper limit of approximately 150 mm.

A kit for analyzing a plurality of sorbent coated fibers comprising a plurality of sorbent coated fibers with an average length and an average diameter to permit multiple exposure of the plurality of sorbent coated fibers to a plurality of different temperature gasses from a desorption ionization source, a holder for positioning the plurality of sorbent coated fibers such that the plurality of sorbent coated fibers are separated at least by a distance, where the holder or other means enables contact between the plurality of sorbent coated fibers and one or more samples and a means to adjust a position of one or both the holder and the plurality of sorbent coated fibers such that a plurality of different temperatures of a carrier gas from a desorption ionization source are directed at one or more target areas on the plurality of sorbent coated fibers, where the distance is between a lower limit of approximately 1 mm and an upper limit of approximately 10 mm, where the average length is between a lower limit of approximately 4 mm and an upper limit of approximately 150 mm, where the average diameter is between a lower limit of approximately 0.05 mm and an upper limit of approximately 2 mm.

A kit for analyzing a plurality of sorbent coated fibers comprising a plurality of sorbent coated fibers with an average length and an average diameter to permit multiple exposure of the plurality of sorbent coated fibers to a plurality of different temperature gasses from a desorption ionization source, a holder for positioning the plurality of sorbent coated fibers such that the plurality of sorbent coated fibers are separated at least by a distance, where the holder or other means enables contact between the plurality of sorbent coated fibers and one or more samples and a means to adjust a position of one or both the holder and the plurality of sorbent coated fibers such that a plurality of different temperatures of a carrier gas from a desorption ionization source are directed at one or more target areas on the plurality of sorbent coated fibers, where the distance is between a lower limit of approximately 1 mm and an upper limit of approximately 10 mm, where the average length is between a lower limit of approximately 4 mm and an upper limit of approximately 150 mm, where the average diameter is between a lower limit of approximately 0.05 mm and an upper limit of approximately 2 mm, where one or more of the plurality of sorbent coated fibers is made up of one or more materials selected from the group consisting of C-18, PDMS/divinyl-benzene, PDMS, C-8 and C-4.

A kit for analyzing a sorbent coated fiber comprising a sorbent coated fiber of a length and a diameter to permit multiple exposure of the sorbent coated fiber to a plurality of different temperature gasses from a desorption ionization source, a reagent fiber containing reactive chemicals, and a holder for positioning the sorbent coated fiber at a distance from the reagent fiber, where the holder is adapted to position one or both the sorbent coated fiber and the reagent fiber to direct a plurality of different temperatures of a carrier gas from a desorption ionization source at a target area on one or both the sorbent coated fiber and the reagent fiber to analyze molecules present on the one or both the sorbent coated fiber and the reagent fiber.

A kit for analyzing a sorbent coated fiber comprising a sorbent coated fiber of a length and a diameter to permit multiple exposure of the sorbent coated fiber to a plurality of different temperature gasses from a desorption ionization source, a reagent fiber containing reactive chemicals, and a holder for positioning the sorbent coated fiber at a distance from the reagent fiber, where the holder is adapted to position one or both the sorbent coated fiber and the reagent fiber to direct a plurality of different temperatures of a carrier gas from a desorption ionization source at a target area on one or both the sorbent coated fiber and the reagent fiber to analyze molecules present on the one or both the sorbent coated fiber and the reagent fiber, where the distance is between a lower limit of approximately 1 mm and an upper limit of approximately 10 mm.

A kit for analyzing a sorbent coated fiber comprising a sorbent coated fiber of a length and a diameter to permit multiple exposure of the sorbent coated fiber to a plurality of different temperature gasses from a desorption ionization source, a reagent fiber containing reactive chemicals, and a holder for positioning the sorbent coated fiber at a distance from the reagent fiber, where the holder is adapted to position one or both the sorbent coated fiber and the reagent fiber to direct a plurality of different temperatures of a carrier gas from a desorption ionization source at a target area on one or both the sorbent coated fiber and the reagent fiber to analyze molecules present on the one or both the sorbent coated fiber and the reagent fiber, where the distance is between a lower limit of approximately 1 mm and an upper limit of approximately 10 mm, where the length is between a lower limit of approximately 4 mm and an upper limit of approximately 150 mm.

A kit for analyzing a sorbent coated fiber comprising a sorbent coated fiber of a length and a diameter to permit multiple exposure of the sorbent coated fiber to a plurality of different temperature gasses from a desorption ionization source, a reagent fiber containing reactive chemicals, and a holder for positioning the sorbent coated fiber at a distance from the reagent fiber, where the holder is adapted to position one or both the sorbent coated fiber and the reagent fiber to direct a plurality of different temperatures of a carrier gas from a desorption ionization source at a target area on one or both the sorbent coated fiber and the reagent fiber to analyze molecules present on the one or both the sorbent coated fiber and the reagent fiber, where the distance is between a lower limit of approximately 1 mm and an upper limit of approximately 10 mm, where the length is between a lower limit of approximately 4 mm and an upper limit of approximately 150 mm, where the diameter is between a lower limit of approximately 0.05 mm and an upper limit of approximately 2 mm.

A method of ionizing a sample on a sorbent coated fiber comprising the steps of receiving a sorbent coated fiber of a length and a diameter to permit multiple exposure of the sorbent coated fiber, contacting the sorbent coated fiber with the sample, directing a first carrier gas with a first temperature from a desorption ionization source at a first target area on the sorbent coated fiber to generate a plurality of first sample ions, and directing a second carrier gas with a second temperature at a second target area on the sorbent coated fiber to generate a plurality of second sample ions directing one or both the plurality of first sample ions and the plurality of second sample ions into an analysis instrument.

A method of analyzing a sorbent coated fiber comprising the steps of receiving a sorbent coated fiber of a length and a diameter to permit multiple exposure of the sorbent coated fiber to a plurality of different temperature gasses from a desorption ionization source, bringing the sorbent coated fiber into contact with a sample, directing a carrier gas with a first temperature from the desorption ionization source at a first target area on the sorbent coated fiber to generate a plurality of first sample ions, directing a carrier gas with a second temperature from the desorption ionization source at a second target area on the sorbent coated fiber to generate a plurality of second sample ions, directing one or both the plurality of first sample ions and the plurality of second sample ions into an analysis instrument and analyzing one or both the plurality of first sample ions and the plurality of second sample ions.

While the systems, methods, and devices have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and devices provided herein. Additional advantages and modifications will readily be apparent to those skilled in the art. Therefore, the invention, in its broader aspects, is not limited to the specific details, the representative system, method or device, and illustrative examples shown and described. Accordingly, departures may be made from such details without departing from the spirit or scope of the applicant's general inventive concept. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

What is claimed is:

1. A system comprising:
one or more fibers, where at least one fiber includes a sorbent coating to permit exposure of the sorbent coating to two or more independent target areas of ionizing species, where the sorbent coating extends a width on the at least one fiber or a diameter around the at least one fiber between:
a lower limit of approximately 0.05 mm; and
an upper limit of approximately 2 mm;
an ionization source adapted to direct one or more ionizing species at one of the two or more independent target areas of the at least one fiber thereby generating a plurality of sample ions from one of the two or more independent target areas; and
an analyzer, adapted to analyze the plurality of sample ions.

2. The system of claim 1, further comprising:
a holder to stabilize a position of the one or more fibers such that the one or more fibers are separated at least by a distance; and
an adjuster to set the position of the holder such that the one or more ionizing species from the ionization source are directed at one of the two or more independent target areas of the at least one fiber.

3. The system of claim 2, where the distance is between:
a lower limit of approximately 1 mm; and
an upper limit of approximately 10 mm.

4. The system of claim 1, where the sorbent coating extends a distance on the at least one fiber, where the distance is between:
a lower limit of approximately 4 mm; and
an upper limit of approximately 150 mm.

5. The system of claim 1, where the sorbent coating comprises one or more materials selected from the group consisting of C-18, PDMS/divinyl-benzene, PDMS, cation exchange, C-8, C-4, carbon, functionalized carbon, tenax and inorganic materials.

6. The system of claim 1, where the one or more ionizing species are generated by a DART source, where the one or more ionizing species are selected from the group consisting of neutral excited atoms or molecules of helium, nitrogen, oxygen, neon, argon, krypton, and xenon.

7. The system of claim 6, further comprising a heater to heat the one or more ionizing species to between:
a lower limit of approximately 270° K; and
an upper limit of approximately 600° K.

8. The system of claim 1, where the ionization source is selected from the group consisting of DART, DESI, MALDI, UV laser, IR laser, atmospheric pressure chemical ionization, directed electrospray, electrospray, dielectric barrier discharge, and flowing after-glow plasma source.

9. The system of claim 1, further comprising an automated sampler where a position of the one or more fibers can be adjusted robotically to allow analysis of one or more independent target areas of one or more of the one or more fibers with one or more ionizing species.

10. The system of claim 1, further comprising a second ionization source, where the second ionization source directs a second ionizing species at one of the two or more independent target areas.

11. The system of claim 10, where one or both the ionization source and the second ionization source is an electrospray ionization source.

12. The system of claim 10, where the ionization source is the same as the second ionization source.

13. A system comprising:
one or more fibers, where at least one fiber includes a sorbent coating with length and one or both a width and a diameter to permit exposure of the sorbent coating to a first target area and a second target area, where ionizing species directed to the first target area do not overlap with ionizing species directed to the second target area, where the one or both the width and the diameter of the sorbent coating is between:
a lower limit of approximately 0.05 mm, and
an upper limit of approximately 2 mm;
an ionization source adapted to direct one or more ionizing species at one or both the first target area and the second target area of the at least one fiber thereby generating a plurality of sample ions from one or both the first target area and the second target area; and
an analyzer, adapted to analyze the plurality of sample ions.

14. The system of claim 13, further comprising:
a holder to stabilize a position of the one or more fibers such that the one or more fibers are separated at least by a distance; and
an adjuster to set the position of the holder such that the one or more ionizing species from the ionization source are directed at one or both the first target area and the second target area of the at least one fiber.

15. The system of claim 13, where the length of the sorbent coating is between;
a lower limit of approximately 4 mm, and
an upper limit of approximately 150 mm.

16. The system of claim 13, where the sorbent coating comprises one or more materials selected from the group consisting of C-18, PDMS/divinyl-benzene, PDMS, cation exchange, C-8, C-4, carbon, functionalized carbon, tenax and inorganic materials.

17. A system comprising:
one or more fibers, where at least one fiber includes a sorbent coating with length and a width or diameter to permit exposure of the sorbent coating to two or more independent target areas of ionizing species;
a first ionization source adapted to direct one or more ionizing species at one or more independent target areas of the at least one fiber thereby generating a first plurality of sample ions from the one or more independent target areas;
a second ionization source adapted to direct one or more ionizing species at one or more independent target areas of the at least one fiber thereby generating a second plurality of sample ions from the one or more independent target areas, where one or both the first ionization source and the second ionization source are selected from the group consisting of DART, DESI, MALDI, UV laser, IR laser, atmospheric pressure chemical ionization, directed electrospray, electrospray, dielectric barrier discharge, and flowing afterglow plasma source; and
an analyzer to analyze one or both the first plurality of sample ions and the second plurality of sample ions.

18. The system of claim 17, where the sorbent coating includes a reactive chemical.

19. A system comprising:
one or more fibers, where at least one fiber includes a sorbent coating to permit exposure of the sorbent coating to a first target area and a second target area;
a first ionization source adapted to direct a first ionizing species at the first target area thereby generating a first plurality of sample ions;

a second ionization source, where the second ionization source directs a second ionizing species at the second target area thereby generating a second plurality of sample ions; and an analyzer, adapted to analyze one or both the first plurality of sample ions and the second plurality of sample ions.

20. The system of claim 19, where one or both the first ionization source and the second ionization source is an electrospray ionization source.

21. A system comprising:

one or more fibers, where at least one fiber includes a sorbent coating with length and one or both a width and a diameter to permit exposure of the sorbent coating to a first target area and a second target area, where ionizing species directed to the first target area do not overlap with ionizing species directed to the second target area, where the length of the sorbent coating is between;

a lower limit of approximately 4 mm, and an upper limit of approximately 150 mm;

an ionization source adapted to direct one or more ionizing species at one or both the first target area and the second target area of the at least one fiber thereby generating a plurality of sample ions from one or both the first target area and the second target area; and an analyzer, adapted to analyze the plurality of sample ions.

22. The system of claim 21, where the sorbent coating extends a width on the at least one fiber or a diameter around the at least one fiber between:

a lower limit of approximately 0.05 mm; and an upper limit of approximately 2 mm.

* * * * *